United States Patent
Holden et al.

(10) Patent No.: US 12,269,037 B2
(45) Date of Patent: Apr. 8, 2025

(54) DROPLET INTERFACES IN ELECTRO-WETTING DEVICES

(71) Applicant: Oxford Nanopore Technologies PLC, Oxford (GB)

(72) Inventors: Matthew Holden, Cambridge, MA (US); Ken Healy, Cambridge, MA (US)

(73) Assignee: Oxford Nanopore Technologies PLC, Oxford (GB)

( * ) Notice: Subject to any disclaimer, the term of this patent is extended or adjusted under 35 U.S.C. 154(b) by 971 days.

(21) Appl. No.: 17/057,910

(22) PCT Filed: May 24, 2019

(86) PCT No.: PCT/US2019/033957
§ 371 (c)(1),
(2) Date: Nov. 23, 2020

(87) PCT Pub. No.: WO2019/227013
PCT Pub. Date: Nov. 28, 2019

(65) Prior Publication Data
US 2021/0205814 A1 Jul. 8, 2021

Related U.S. Application Data

(60) Provisional application No. 62/675,943, filed on May 24, 2018.

(51) Int. Cl.
*B01L 3/00* (2006.01)
*G01N 33/487* (2006.01)

(52) U.S. Cl.
CPC .. *B01L 3/502792* (2013.01); *G01N 33/48728* (2013.01); *B01L 2200/10* (2013.01);
(Continued)

(58) Field of Classification Search
CPC ........... B01L 3/502792; B01L 2200/10; B01L 2200/143; B01L 2300/0645;
(Continued)

(56) References Cited

U.S. PATENT DOCUMENTS

| 6,565,727 B1 | 5/2003 | Shenderov |
| 6,911,132 B2 | 6/2005 | Pamula et al. |

(Continued)

FOREIGN PATENT DOCUMENTS

| EP | 1 053 055 B1 | 7/2003 |
| GB | 2533952 A | 7/2016 |

(Continued)

OTHER PUBLICATIONS

Invitation to Pay Additional Fees dated Aug. 14, 2019 for International Application No. PCT/US2019/033957.

(Continued)

*Primary Examiner* — Jennifer Wecker
(74) *Attorney, Agent, or Firm* — Wolf, Greenfield & Sacks, P.C.

(57) ABSTRACT

Droplet interfaces are formed between droplets in an electro-wetting device comprising an array of actuation electrodes. Actuation signals are applied to selected actuation electrodes to place the droplets into an energised state in which the shape of the droplets is modified compared to a shape of the droplets in a lower energy state and to bring the two droplets into proximity. The actuation signals are then changed to lower the energy of the droplets into the lower energy state so that the droplets relax into the gap and the two droplets contact each other thereby forming a droplet interface. The use of sensing electrodes in the device permit electrical current measurements across the droplet interface. The sensing electrodes can be used for either (i) applying a reference signal during droplet actuation or (ii) recording electrical (Continued)

current measurements. Two or more electrodes are configurable to lyse cells within a droplet positioned over said electrodes.

20 Claims, 12 Drawing Sheets

(52) U.S. Cl.
CPC . *B01L 2200/143* (2013.01); *B01L 2300/0645* (2013.01); *B01L 2300/165* (2013.01); *B01L 2400/0424* (2013.01); *B01L 2400/0427* (2013.01)

(58) Field of Classification Search
CPC ......... B01L 2300/165; B01L 2300/161; B01L 2400/0424; B01L 2400/0427; G01N 33/48728; G01N 33/48721; C12M 23/16; C12M 47/06; C12Q 1/6806; C12N 13/00
See application file for complete search history.

(56) References Cited

U.S. PATENT DOCUMENTS

| | | | |
|---|---|---|---|
| 6,916,488 | B1 | 7/2005 | Meier et al. |
| 6,942,169 | B2 | 9/2005 | Sparks |
| 7,163,612 | B2 | 1/2007 | Sterling et al. |
| 8,653,832 | B2 | 2/2014 | Hadwen et al. |
| 9,914,135 | B2 | 3/2018 | Manaresi et al. |
| 2008/0302431 | A1 | 12/2008 | Marchand et al. |
| 2009/0155902 | A1* | 6/2009 | Pollack .................. C12N 13/00 435/372.2 |
| 2010/0194408 | A1 | 8/2010 | Sturmer et al. |
| 2010/0203521 | A1 | 8/2010 | Klapperich et al. |
| 2012/0279298 | A1* | 11/2012 | Etheredge, III .. B01L 3/502746 73/431 |
| 2013/0217113 | A1 | 8/2013 | Srinivasan et al. |
| 2014/0202863 | A1 | 7/2014 | Hadwen |
| 2014/0216559 | A1* | 8/2014 | Foley ................ B01L 3/502792 137/803 |
| 2015/0265994 | A1* | 9/2015 | Hyde ................... B01J 19/0046 506/40 |
| 2015/0285781 | A1* | 10/2015 | Heron .................. C12Q 1/6869 525/186 |
| 2015/0306599 | A1* | 10/2015 | Khandros ............... B03C 5/005 204/547 |
| 2016/0305906 | A1 | 10/2016 | Amos et al. |
| 2018/0074013 | A1* | 3/2018 | Lee ................... B01L 3/502792 |
| 2018/0095067 | A1* | 4/2018 | Huff ................. G01N 33/48721 |

FOREIGN PATENT DOCUMENTS

| | | |
|---|---|---|
| JP | 2008-504124 A | 2/2008 |
| JP | 2014-140841 A | 8/2014 |
| JP | 2018-510677 A | 4/2018 |
| WO | WO 2008/012552 A1 | 1/2008 |
| WO | WO 2010/086603 A1 | 8/2010 |
| WO | WO 2011/067559 A1 | 6/2011 |
| WO | WO 2012/107778 A1 | 8/2012 |
| WO | WO 2012/164270 A1 | 12/2012 |
| WO | WO 2013/041878 A1 | 3/2013 |
| WO | WO 2013/083983 A1 | 6/2013 |
| WO | WO 2013/121224 A1 | 8/2013 |
| WO | WO 2013/153359 A1 | 10/2013 |
| WO | WO 2014/064443 A2 | 5/2014 |
| WO | WO 2014/064444 A1 | 5/2014 |
| WO | WO 2015/140535 A1 | 9/2015 |
| WO | WO 2015/150786 A1 | 10/2015 |
| WO | WO 2016/034591 A2 | 3/2016 |
| WO | WO 2016-123608 A2 | 8/2016 |
| WO | WO 2017/004504 A1 | 1/2017 |
| WO | WO 2017/149316 A1 | 9/2017 |
| WO | WO 2017/149317 A1 | 9/2017 |
| WO | WO 2017/149318 A1 | 9/2017 |
| WO | WO 2018/100370 A1 | 6/2018 |

OTHER PUBLICATIONS

International Search Report and Written Opinion dated Oct. 15, 2019 for International Application No. PCT/US2019/033957.

International Preliminary Report on Patentability dated Dec. 3, 2020 for International Application No. PCT/US2019/033957.

Abonnenc et al., Lysis-on-chip of single target cells following forced interaction with CTLs or NK cells on a dielectrophoresis-based array. J Immunol. Oct. 1, 2013;191(7):3545-52. doi: 10.4049/jimmunol.1300890. Epub Sep. 4, 2013.

Altschul et al., Basic local alignment search tool. J Mol Biol. Oct. 5, 1990;215(3):403-10. doi: 10.1016/S0022-2836(05)80360-2.

Altschul, S.F., A protein alignment scoring system sensitive at all evolutionary distances. J Mol Evol. Mar. 1993;36(3):290-300. doi: 10.1007/BF00160485.

Boza et al., Deep recurrent neural networks for base calling in MinION nanopore reads. PLoS One. Jun. 5, 2017;12(6):e0178751. doi: 10.1371/journal.pone.0178751.

Devereux et al., A comprehensive set of sequence analysis programs for the VAX. Nucleic Acids Res. Jan. 11, 1984;12(1 Pt 1):387-95. doi: 10.1093/nar/12.1part1.387.

Fan et al., Cross-scale electric manipulations of cells and droplets by frequency-modulated dielectrophoresis and electro wetting. Lab Chip. Aug. 2008;8(8):1325-31. doi: 10.1039/b803204a. Epub May 28, 2008.

Gilboa et al., Optical sensing and analyte manipulation in solid-state nanopores. Analyst. Jul. 21, 2015;140(14):4733-47. doi: 10.1039/c4an02388a. Epub Feb. 16, 2015.

Holden et al., Functional bionetworks from nanoliter water droplets. J Am Chem Soc. Jul. 11, 2007;129(27):8650-5. doi: 10.1021/ja072292a.

Issadore, D.A., Hybrid integrated circuit/microfluidic chips for the control of living cells and ultra-small biomimetic containers. Doctoral Dissertation. Harvard University. May 2009. Accessible via meso.seas.harvard.edu/theses/issadore.pdf. 161 pages.

Langecker et al., Synthetic lipid membrane channels formed by designed DNA nanostructures. Science. Nov. 16, 2012;338(6109):932-6. doi: 10.1126/science.1225624.

Leptihn et al., Constructing droplet interface bilayers from the contact of aqueous droplets in oil. Nat Protoc. Jun. 2013;8(6):1048-57. doi: 10.1038/nprot.2013.061. Epub May 2, 2013.

Li et al., Cellular dielectrophoresis coupled with single-cell analysis. Anal Bioanal Chem. Apr. 2018;410(10):2499-2515. doi: 10.1007/s00216-018-0896-y. Epub Feb. 23, 2018.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010. Author Manuscript, 9 pages.

Martel et al., Handling of artificial membranes using electrowetting-actuated droplets on a microfluidic device combined with integrated pA-measurements. Biomicrofluidics. Mar. 2012;6(1):12813-128137. doi: 10.1063/1.3665719. Epub Mar. 15, 2012.

Montal et al., Formation of bimolecular membranes from lipid monolayers and a study of their electrical properties. Proc Natl Acad Sci USA. Dec. 1972;69(12):3561-6. doi: 10.1073/pnas.69.12.3561.

Pohl et al., Dielectrophoresis of cells. Biophys J. Sep. 1971;11(9):711-27. doi: 10.1016/S0006-3495(71)86249-5.

Potter, H., Transfection by electroporation. Curr Protoc Mol Biol. May 2003;Chapter 9:Unit 9.3. doi: 10.1002/0471142727. mb0903s62. Author Manuscript, 12 pages.

Poulos et al., Electrowetting on dielectric-based microfluidics for integrated lipid bilayer formation and measurement. Appl. Phys. Lett. Jul. 2009;95:1;013706(1-3). doi: https://doi.org/10.1063/1.3167283.

(56) References Cited

OTHER PUBLICATIONS

Soni et al., Synchronous optical and electrical detection of biomolecules traversing through solid-state nanopores. Rev Sci Instrum. Jan. 2010;81(1):014301. doi: 10.1063/1.3277116.

Valley et al., A unified platform for optoelectrowetting and optoelectronic tweezers. Lab Chip. Apr. 7, 2011;11(7):1292-7. doi: 10.1039/c01c00568a. Epub Feb. 11, 2011. Erratum in: Lab Chip. Dec. 21, 2011;11(24):4279. Ningpei, Shao [corrected to Pei, Shao Ning].

Young et al., Development of an integrated chip for automatic tracking and positioning manipulation for single cell lysis. Sensors (Basel). 2012;12(3):2400-13. doi: 10.3390/s120302400. Epub Feb. 23, 2012.

PCT/US2019/033957, Aug. 14, 2019, Invitation to Pay Additional Fees.

PCT/US2019/033957, Oct. 15, 2019, International Search Report and Written Opinion.

PCT/US2019/033957, Dec. 3, 2020, International Preliminary Report on Patentability.

* cited by examiner

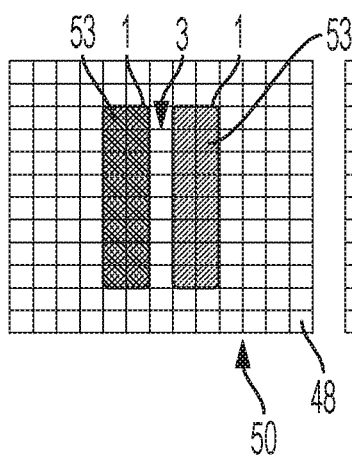
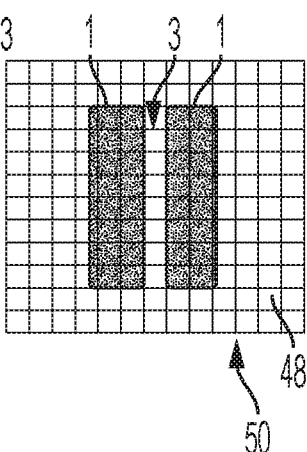
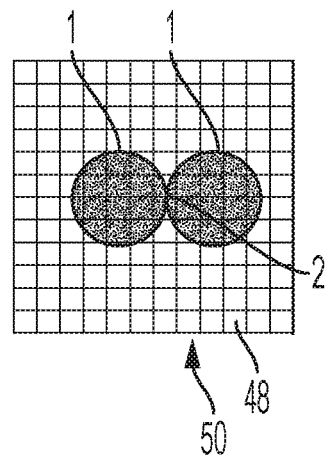
FIG. 10  FIG. 11  FIG. 12
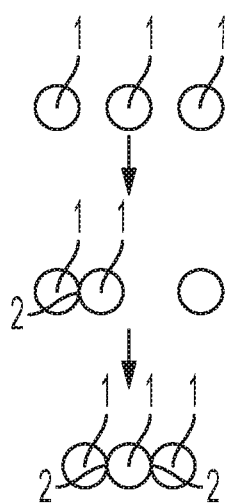
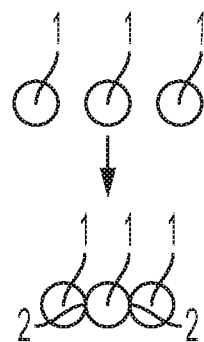
FIG. 13  FIG. 14
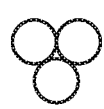
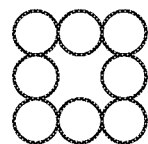
FIG. 15  FIG. 16

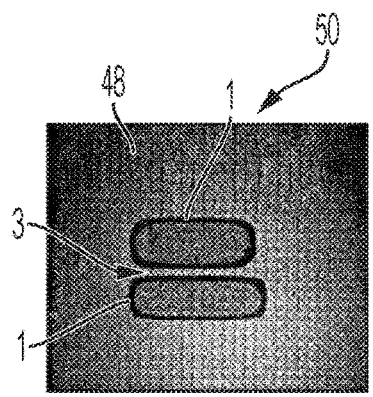
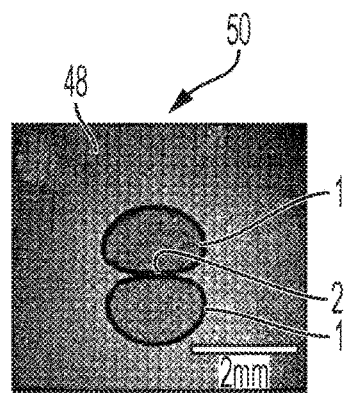
FIG. 17A    FIG. 17B
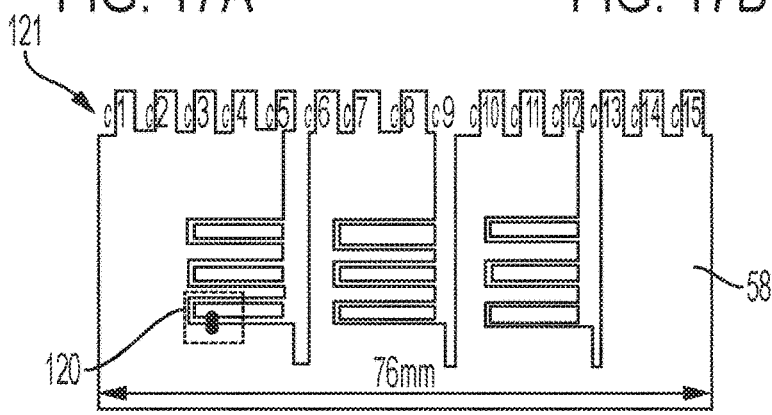
FIG. 18
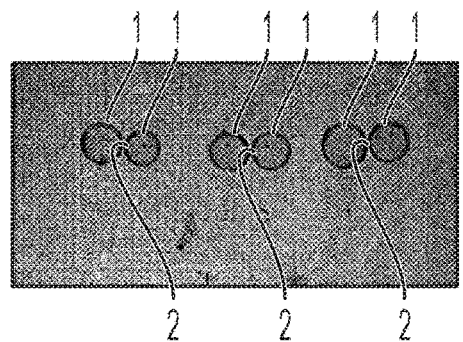
FIG. 19
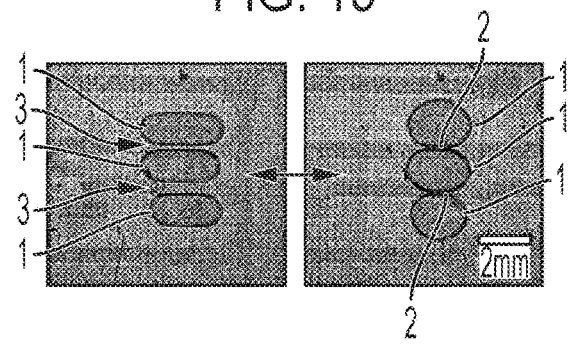
FIG. 20

DROPLET INTERFACES IN ELECTRO-WETTING DEVICES

RELATED APPLICATIONS

This Application is a national stage filing under 35 U.S.C. § 371 of international application number PCT/US2019/033957, filed May 24, 2019, which claims the benefit under 35 U.S.C. § 119(e) of U.S. Provisional Application No. 62/675,943, filed May 24, 2018, each of which is incorporated by reference in its entirety.

TECHNICAL FIELD

Electro-wetting devices and related systems and uses are generally described. In some aspects, the present invention relates to electro-wetting devices and their use to form droplet interfaces between droplets of liquid in a fluid medium. In some aspects, the present invention relates to electro-wetting devices and their use in making measurements on droplet interfaces formed using electro-wetting. In other aspects, the present invention relates to the preparation of samples using electrowetting devices. Electro-wetting devices, for example electro-wetting on dielectric (EWOD) devices, are known for manipulating droplets of liquid in a fluid medium.

BACKGROUND

Considering this in more detail, electro-wetting on dielectric is a well-known technique for manipulating droplets of fluid by the application of an electric field, for example as disclosed in US2016/0305906. Example configurations and operation of EWOD devices are described in the following documents. U.S. Pat. No. 6,911,132 discloses a two-dimensional EWOD array to control the position and movement of droplets in two dimensions. U.S. Pat. No. 6,565,727 discloses methods for other droplet operations including the splitting and merging of droplets, and the mixing together of droplets of different materials. U.S. Pat. No. 7,163,612 describes how an active matrix (AM) arrangement based on thin film electronics including thin-film transistors (TFT) may be used to control the addressing of voltage pulses to an EWOD device, using circuit arrangements similar to those employed in AM display technologies. Devices of this general type may be referred to as AM-EWOD devices.

It has been proposed to use EWOD devices to manipulate such droplets to form droplet interfaces between droplets, for example comprising a membrane of amphipathic molecules. That provides a potentially useful system for studying the droplet interfaces themselves, and also processes occurring at the droplet interfaces. In one example having particular interest, such processes may involve insertion of a transmembrane pore, and subsequent measurement of properties such as ion current flow that may be dependent on interaction of an analyte with such a transmembrane pore.

Membranes of amphipathic molecules, for example artificial planar lipid bilayers may serve as simplified models of biological membranes and are widely used for the study of various processes, including the characterisation of transmembrane pores, such as transmembrane protein pores, for example ion-channels. Ion-channels are a diverse group of transmembrane protein pores that in biology selectively control the movement of specific ions across cell membranes, establishing voltage and electrochemical gradients that are fundamental to a wide variety of biological processes.

Single-channel recording (SCR) of individual protein pores is a powerful means of studying channel protein function. Single-channel recording measures changes in ion-current through single protein channels, and can examine voltage dependence, gating behaviour, ligand binding affinity, and ion selectivity at the single-molecule level. Various methods may be employed to form lipid bilayers such as disclosed by Montal, M. & Mueller, P. 1972. Proceedings of the National Academy of Sciences of the United States of America 69, 3561-3566). Although widely used, planar lipid bilayers are difficult to prepare, and their short lifetime prohibits their use in many situations.

Thus other membranes of amphipathic molecules have been proposed. Alternatives to planar lipid bilayers are disclosed, for example, WO-2008/012552 which discloses a method of forming bilayers of amphipathic molecules uses droplets of aqueous solution in a hydrophobic medium such as oil.

Arrays of individual suspended membranes of amphipathic molecules containing respective ion channel protein pores or nanopores may be provided, for example disclosed in WO-2014/064443. Ion current between two aqueous solutions provided at either side of the amphipathic membrane may be measured in order to characterise an analyte such as polynucleotide and commercial devices such as the MinION™ comprising a nanopore array that is able to determine a polynucleotide sequence are sold by Oxford Nanopore Technologies Ltd.

Droplet interfaces between droplets in contact with one another are therefore an alternative way of forming membranes of amphipathic molecules. Such a membrane formed by a bilayer of amphipathic molecules may be referred to as a droplet interface bilayer (DIB). Multiple membranes can be formed at the interface between multiple pairs of droplets. Techniques for forming DIBs are disclosed for example in Leptihn et al, Nature Protocols 8, 1048-1057 (2013) and DIBs may be used for the study of transmembrane pores inserted therein. For example, Martel et al., Biomicrofluidics 6, 012813 (2012) discloses a microfluidic device for forming droplet interface bilayers into which a protein channel was inserted. Gold microwires were deposited onto the substrate including the actuation electrodes upon which Ag/AgCl pads were provided in order to make electrical contact with each droplet in order to carry out measurements of ion current flow through the membrane channel.

SUMMARY

In some aspects, the present invention relates to electro-wetting devices and their use to form droplet interfaces between droplets of liquid in a fluid medium. In some aspects, the present invention relates to electro-wetting devices and their use in making measurements on droplet interfaces formed using electro-wetting. In other aspects, the present invention relates to the preparation of samples using electrowetting devices. Electro-wetting devices, for example electro-wetting on dielectric (EWOD) devices, are known for manipulating droplets of liquid in a fluid medium.

The subject matter of the present invention involves, in some cases, interrelated products, alternative solutions to a particular problem, and/or a plurality of different uses of one or more systems and/or articles.

The first aspect of the present invention is concerned with methods and devices for forming a droplet interface in an electro-wetting device.

According to a first aspect of the present invention, there is provided a method of forming a droplet interface in an electro-wetting device, the electro-wetting device comprising: an array of actuation electrodes; an insulator layer covering the actuation electrodes and having an outermost hydrophobic surface; disposed on the hydrophobic surface, a fluid medium and two droplets comprising liquid in the fluid medium, one of the liquid and the fluid medium being polar, and the other of the liquid and the fluid medium being apolar, whereby the actuation electrodes are capable of electro-wetting the droplets when actuation signals are applied thereto, the method comprising: applying actuation signals to selected actuation electrodes to place one or both of the two droplets in an energised state in which the shape of said one or both droplets is modified compared to when in a lower energy state and to bring the two droplets into proximity with a gap therebetween, the gap being chosen such that the two droplets do not contact each other when one or both are in the energised state and contact each other to form a droplet interface when in the lower energy state; and changing the actuation signals applied to the actuation electrodes to lower the energy of said one or both droplets into the lower energy state so that said one or both droplets relax into the gap and the two droplets contact each other thereby forming a droplet interface.

In some embodiments, this method is applied to an electro-wetting device that comprises an array of actuation electrodes and an insulator layer covering the actuation electrodes and having an outermost hydrophobic surface. In some embodiments, in such an electro-wetting device, a fluid medium and two droplets comprising liquid in the fluid medium may be disposed on the hydrophobic surface. In some embodiments, the actuation electrodes are capable of electro-wetting the droplets when actuation signals are applied thereto, thereby allowing manipulation of the droplets by selection of the actuation signals.

In some embodiments, the method provides a reliable technique for forming a droplet interface between two droplets. With the present method the actuation signals are applied to the actuation electrodes in two phases, in some embodiments. In some embodiments, in the initial phase, the applied actuation signals have a pattern selected to place one or both of the two droplets in an energised stated. As a result, in some embodiments, the shape of one or both droplets is modified compared to when in a lower energy state. In such an energised state, in some embodiments, the two droplets are brought into proximity with a gap therebetween. In some embodiments, the gap is chosen such that the two droplets do not contact each other when one or both are in the energised state and contact each other to form a droplet interface when in the lower energy state.

In a subsequent phase, in some embodiments, the applied actuation signals are changed to lower the energy of said one or both droplets into a lower energy state. As a result, in some embodiments, one or both droplets relax into the gap and the two droplets contact each other. In some embodiments, a droplet interface is thereby formed between the two droplets. Thus, in some embodiments, movement of a surface of the one or both droplets is caused by relaxation of the energised state, which is a passive process.

In some embodiments, this process improves the reliability of formation of the droplet interface, compared to attempting to bring two droplets into contact directly by applying actuation signals that move the entire droplets towards one another. While such methods might be possible in principle, the droplets have a tendency to fuse (i.e. merge) and it is difficult to maintain the interface between the droplets, in some embodiments.

While the method may be applied, in some embodiments, by placing a single one of the two droplets in an energised state, preferably both droplets are placed in the energised state. As a result, in some embodiments, the surfaces of both droplets relax into the gap and contact each other to form the droplet interface. In this manner, in some embodiments, relaxation of both droplets is used to form the droplet interface, which further increases the reliability of formation.

In some embodiments, in the energised state of the one or both droplets, any shape of the droplets may be selected that allows the desired relaxation of the surface to form the droplet interface. While various shapes are possible, advantageously the shape of the droplet in the energised state as viewed in the plane of the electro-wetting device is elongate, in some embodiments. Similarly, in some embodiments, the shape of the contact line of the droplet in the energised state is elongate. In that case, the gap between droplets may extend along a major length of the elongate shape, in some embodiments, so that on relaxation, a surface of the droplet extending along the major length may move into the gap to contact the other droplet.

Where an elongated shape is used, the shape of the droplet in the energised state may have an aspect ratio of at least 2:1, preferably at least 4:1 or at least 8:1, in some embodiments. In some embodiments, increasing the aspect ratio increases the degree of movement of the surface of the at least one droplet, which assists bringing the droplets into contact.

In some embodiments, during the step of applying actuation signals to the actuation electrodes, the two droplets may be brought into proximity with the centroids of the two droplets, separated by a distance less than the combined radii of the droplets, along a line between the two centroids in the lower energy state of the droplets.

In some embodiments, the method may be applied with advantage to an electro-wetting device wherein the area enclosed by the contact line of the droplets in the lower energy state covers at least two actuation electrodes, preferably at least 5 actuation electrodes, at least 10 actuation electrodes or at least 20 actuation electrodes. In the design of the electro-wetting device, in some embodiments, the more actuation electrodes a droplet covers the better the resolution of the control of the shape in the energised state of the droplet. That in turn allows the degree of movement of the surface of the at least one droplet to be increased, which assists bringing the droplets into contact, in some embodiments.

In some embodiments, the actuation signals that are selected to energise the one or more droplets may be alternating (AC) actuation voltage signals. In some embodiments, the use of AC actuation signals in an electro-wetting device is known to be advantageous for manipulating droplets. In that case, preferably, the step of changing the actuation signals applied to the selected actuation electrodes may comprise applying DC potentials or floating potentials to the selected actuation electrodes in place of the AC actuation signals. In some embodiments, this improves the reliability of formation of the droplet interfaces, because the DC potentials or floating potentials are less likely to rupture the droplet interface than if AC actuation signals were maintained.

In some embodiments, the method may be applied to an electro-wetting device wherein the insulator layer comprises a layer of electrically insulating material coated by a hydrophobic material that forms said hydrophobic surface.

In some embodiments, the method may be applied to an electro-wetting device that further comprises a second substrate facing the hydrophobic surface of the insulator layer, wherein the second substrate is coated by a hydrophobic material forming a further hydrophobic surface facing the hydrophobic surface of the insulator layer. In this case, the droplets may be disposed on the further hydrophobic surface of the hydrophobic layer as well as the hydrophobic surface of the insulator layer. In this manner, in some embodiments, the droplets are sandwiched between the two substrates, which constrains the shape of the droplets. In some embodiments, this improves the degree of control of the shape of the droplets between the energised state and lower energy state, which in turn improves the reliability of the formation of droplet interfaces.

Furthermore, in some embodiments, the second substrate may support sensor electrodes that make an electrical connection with the droplets between which a droplet interface is formed.

In some embodiments, the method may be applied to an electro-wetting device that further comprises an active matrix arrangement connected to the actuation electrodes.

In some embodiments, the method may be applied to form only a single droplet interface between two droplets, but equally the method may be applied with one or more further droplets disposed on the hydrophobic surface, and the steps of applying and changing actuation signals to the actuation electrodes may be performed to form plural droplet interfaces between plural pairs of droplets.

In some embodiments, after formation of a droplet interface, electrical measurements may be taken between the droplets across the droplet interface. For example, in some embodiments, the electrical measurements may be measurements of ion flow between droplets through a transmembrane pore and/or may be taken while applying a potential difference between the droplets.

Further, according to the first aspect of the present invention, there is provided an electro-wetting device for forming a droplet interface which implements a similar method to that described above, in some embodiments.

The second aspect of the present invention is concerned with making electrical connections to respective droplets in a system of droplets formed in an electro-wetting device and having one or more droplet interfaces between droplets. In some embodiments, such electrical connections may have the purpose of sensing a property of the droplets, such as the size or location of a droplet when performing various droplet operations in the electro-wetting device, or the purpose of taking measurements across a droplet interface.

US-2010/0,194,408 discloses a method, circuit and apparatus for detecting capacitance on a droplet actuator inter alia for determining the presence, partial presence or absence of a droplet at an actuation electrode. U.S. Pat. No. 8,653,832 describes how an impedance (or capacitance) sensing function can be incorporated into the array element circuit of each array element of an AM-EWOD device, wherein the impedance sensor circuit may be used for determining the presence and size of droplets present at each electrode in the array. However, these approaches are limited by the need to obtain signals from the same electrodes to which the actuation signals are applied.

Martel et al., Biomicrofluidics 6, 012813 (2012) discloses a microfluidic device for forming droplet interface bilayers into which a protein channel was inserted, wherein gold microwires were deposited onto the substrate including the actuation electrodes upon which Ag/AgCl pads were provided in order to make electrical contact with each droplet in order to carry out measurements of ion current flowing through the membrane channel. However, this construction is inconvenient and difficult to manufacture, as well as limiting the reliability of taking measurements and limiting the scalability of the technique.

According to a second aspect of the present invention, there is provided an electro-wetting device for taking measurements across a droplet interface, the electro-wetting device comprising: a first substrate supporting an array of actuation electrodes; an insulator layer covering the actuation electrodes and having a hydrophobic surface, a second substrate facing the hydrophobic surface of the insulator layer and supporting at least one set of at least two sensor electrodes, the electro-wetting device being arranged to receive a fluid medium and droplets comprising liquid in the fluid medium disposed on the hydrophobic surface, the actuation electrodes being configured to receive actuation signals for electro-wetting received droplets in order to form at least one system of droplets having one or more droplet interfaces between droplets, and the sensor electrodes of each set being configured to make electrical connections to respective droplets in the at least one system of droplets.

Thus, in the electro-wetting device, sensor electrodes are provided on a second substrate facing the facing the hydrophobic surface of the insulator layer that covers the actuation electrodes, in some embodiments. In some embodiments, such sensor electrodes are arranged in at least one set of at least two sensor electrodes, and the sensor electrodes of each set are configured to make electrical connections to respective droplets in a system of droplets. In some embodiments, this provides a convenient and reliable way to make electrical connections to the droplets.

In some embodiments, the second substrate may be coated by a hydrophobic material forming a further hydrophobic surface facing the hydrophobic surface of the insulator layer. In that case, the electro-wetting device may be arranged to receive the fluid medium and the droplets disposed on the further hydrophobic surface of the hydrophobic layer as well as the hydrophobic surface of the insulator layer. In this manner, in some embodiments, the droplets are sandwiched between the two substrates, which constrains the shape of the droplets. In some embodiments, this improves the degree of control of the droplets by actuation signals applied to the actuation electrodes.

In some embodiments, where second substrate is coated by a hydrophobic material, then the hydrophobic material coating the second substrate may have apertures exposing at least part of the sensor electrodes. In some embodiments, this improves the electrical connection between the sensor electrodes and the droplets.

In some embodiments, the second substrate further supports at least one further electrode, for example for receiving a reference signal while actuation signals are applied to the actuation electrodes for manipulating the droplets.

In some embodiments, the sensor electrodes and the further electrodes, where provided, may be deposited on a surface of the second substrate facing the first substrate. In that case, the further electrodes, where provided, may extend around the sensor electrodes.

In some embodiments, the electro-wetting device may further comprise a control system that is connected to the actuation electrodes and is configured to apply actuation signals to the actuation electrodes for manipulating received droplets.

In some embodiments, the control system may be configured, while applying actuation signals to the actuation electrodes, to apply a reference signal to the sensor electrodes and/or to the further electrodes, where provided.

In some embodiments, the control system may be configured to apply actuation signals to the actuation electrodes selected to form a droplet interface at the interface between two droplets.

In some embodiments, the electro-wetting device may further comprise a sensor system connected to the sensor electrodes and configured to take electrical measurements, for example including impedance measurements, between sensor electrodes that are electrically connected to respective droplets forming a droplet interface therebetween. In some embodiments, such electrical measurements may be taken across a droplet interface between two droplets in a system of droplets.

In some embodiments, the sensor system may be configured to take electrical measurements between respective sensor electrodes that make contact between respective droplets across a droplet interface comprising a membrane of amphipathic molecules having a transmembrane pore inserted therein, for example measurements of ion flow between droplets through a transmembrane pore and/or electrical measurements that are dependent on an analyte that interacts with the transmembrane pore.

In some embodiments, the sensor system may further comprise an analysis system configured to process the electrical measurements to analyse an analyte that interacts with the transmembrane pore. For example, in some embodiments, where the analyte is a polymer comprising polymer units, the analysis system may be configured to process the electrical measurements to derive estimated identities of the polymer units of the polymer.

The third aspect of the present invention is concerned with use of an electro-wetting device to perform experiments on droplet interfaces.

According to a third aspect of the present invention, there is provided an apparatus for performing experiments on droplet interfaces, the apparatus comprising: an electro-wetting device comprising an array of actuation electrodes and an insulator layer covering the actuation electrodes and having an outermost hydrophobic surface, the electro-wetting device being arranged to receive a fluid medium and droplets comprising liquid in the fluid medium disposed on the hydrophobic surface, a control system configured to apply actuation signals to the actuation electrodes selected to manipulate received droplets and to form at least one system of droplets having one or more droplet interfaces between the droplets; and a sensor system configured to take electrical measurements between droplets in a formed system across droplet interfaces.

In some embodiments, such an apparatus is suitable for performing experiments on droplet interfaces.

In some embodiments, the apparatus includes an electro-wetting device in which droplet interfaces may be formed. In some embodiments, the electro-wetting device comprises an array of actuation electrodes and an insulator layer covering the actuation electrodes and having an outermost hydrophobic surface. In some embodiments, the electro-wetting device can receive a fluid medium and droplets comprising liquid in the fluid medium disposed on the hydrophobic surface In some embodiments, the apparatus further includes a control system configured to apply actuation signals to the actuation electrodes selected to manipulate received droplets and to form at least one system of droplets having one or more droplet interfaces between the droplets. Therefore, in some embodiments, use of the control system allows droplet interfaces to be formed in the electro-wetting device.

In some embodiments, the apparatus further includes a sensor system configured to take electrical measurements between droplets in a formed system across droplet interfaces, thereby allowing experiments to be performed on the formed droplet interfaces.

In some embodiments, after formation of a droplet interface, various types of electrical measurements may be taken between the droplets across the droplet interface. For example, in some embodiments, the electrical measurements may be measurements of ion flow between droplets through a transmembrane pore and/or may be taken while applying a potential difference between the droplets.

In some embodiments, the sensor system may further comprise an analysis system configured to process the electrical measurements to analyse an analyte that interacts with the transmembrane pore. For example, in some embodiments, where the analyte is a polymer comprising polymer units, the analysis system may be configured to process the electrical measurements to derive estimated identities of the polymer units of the polymer.

Advantageously, in some embodiments, the control system may be arranged to modify the at least one formed system of droplets in response to the electrical measurements taken by the sensor system. In some embodiments, the ability of the apparatus to modify the formed system of droplets based on feedback from the sensor system provides significant advantages, because it allows the apparatus to perform experiments on droplet interfaces in an adaptive manner.

In some embodiments, the outputs of the sensor system to which the control system responds may include the electrical measurements themselves. In some embodiments, this provides a first type of control of the experiments being performed based on the electrical properties being measured. As the electrical properties are fundamental to the relevant processes such as formation of droplet interfaces and reactions occurring there, this first type of control allows those processes to be considered and adaptively modified, in some embodiments.

Alternatively, in some embodiments, the sensor system comprises an analysis system configured to process the electrical measurements, and said outputs of the sensor system include outputs of the analysis system. In some embodiments, this provides a second type of control of the experiments being performed based on the analysis. As such analysis allows higher level information to be obtained, for example concerning analyte being analysed, this second type of control provides powerful experimental adaption based on the results of the analysis, in some embodiments.

In some embodiments, the types of control which may be performed are extensive, thereby providing a powerful experimental apparatus. Some non-limitative examples are as follows.

In some embodiments, the formed system of droplets may be modified by separating a droplet interface in the system.

In some embodiments, the formed system of droplets may be modified by moving a new droplet into contact with a current droplet in the system of droplets and forming a droplet interface between the new droplet and the current droplet.

In some embodiments, the formed system of droplets may be modified by moving a new droplet into contact with a current droplet in the system of droplets and fusing the new droplet and the current droplet. In that case, it may be that the new droplet does not comprise amphipathic molecules at the interface between the liquid of the droplet and the fluid medium.

Advantageously, in some embodiments, the control system may be arranged to apply actuation signals to the actuation electrodes selected to form plural systems of droplets in parallel. In some embodiments, this allows the apparatus to perform experiments on the plural systems in parallel with each other, thereby increasing the experimental throughput of the apparatus.

In some embodiments, the apparatus may further include a droplet preparation system configured to form droplets disposed on the hydrophobic surface of the electro-wetting device in the fluid medium. In this case, the control system may be configured to control the droplet preparation system to form the droplets. In some embodiments, this increases the experimental power of the apparatus as it allows droplets containing appropriate reagents to be formed for experimental purposes.

In some embodiments, the first to third aspects of the present invention may be implemented together, for example in the same device or apparatus. Accordingly, the preferred features of the first to third aspects of the present invention, some of which are defined in the dependent claims below, may be combined in any combination.

According to a fourth aspect, the invention resides in an apparatus for receiving a droplet having a sample and for lysing said sample to performing experiments on the sample using droplet interfaces, the apparatus comprising: an electro-wetting device comprising an array of actuation electrodes and an insulator layer covering the actuation electrodes and having an outermost hydrophobic surface, the electro-wetting device being arranged to receive a fluid medium and droplets comprising liquid in the fluid medium disposed on the hydrophobic surface; a control system configured to apply actuation signals to the actuation electrodes selected to manipulate received droplets and to form at least one system of droplets having one or more droplet interfaces between the droplets; a lyser, connectable to at least two lysing electrodes, (e.g., a pair; under a droplet), configured to apply a lysing signal to a droplet for lysing a cell within a droplet, wherein the lysing signal is controlled by the control system; and a sensor system configured to take electrical measurements between droplets in a formed system of droplets across droplet interfaces. In some embodiments, the at least two lysing electrodes can be a pair of electrodes upon which a droplet is positioned. In some embodiments, the lysing signal generates an electric field that ruptures cells within the droplet. For example, in some embodiments, the lysing signal can generate an electric field that can rupture a cell within a droplet positioned over the electrodes to which the signal is applied.

In some embodiments, at least two lysing electrodes (e.g., pair) can be measurement electrodes. In some embodiments, at least two lysing electrodes (e.g., pair) can be actuation electrodes.

In some embodiments, the actuation electrodes in the array can be individually controllable. In some embodiments, the control system can be configured to pass a lysing signal via a droplet positioned between or over any two actuation electrodes in the array.

In some embodiments, at least two actuation electrodes in the array can be operable as lysing electrodes configured to provide the lysing signal. In some embodiments, the lysing electrodes can be isolated mechanically and/or electrically from the other electrodes in the array. In some embodiments, the array of electrodes can be configured to manoeuvre a droplet having a sample to and from the lysing electrodes.

In some embodiments, two lysing electrodes can be configured in a lysing zone adjacent or within the array of actuation electrodes, said lysing zone can be isolated from the array of actuation electrodes, and the array of actuation electrodes can be configured to manoeuvre a droplet having a sample to and from the lysing zone.

In some embodiments, the control system can be configured to deactivate and/or isolate the array of actuation electrodes from two or more electrodes that operate as lysing electrodes for a period of time during which a lysing signal is applied to a droplet for lysing a cell within a droplet. In some embodiments, the control system can isolate the actuation electrodes function and/or sensing functions for the period of time and reconnects the array, or switches it on again, before any droplets formed on the hydrophobic surface are disrupted and, therefore, the configuration of droplets on the device maintain or return to their shape or form before isolation occurred.

In some embodiments, the ratio between the length of time that the control system isolates the array of electrodes, and the length of time a lysing signal is applicable to a droplet, can be between about 20:1 and about 2:1,
or can be between about 15:1 and about 5:1,
or can be between about 12:1 and about 8:1. In some embodiments, the lysing signal can be applied to the lysing electrode mid-way during the period of time that the control system isolates or turns-off the actuating and sensing functions connected to the array of electrodes. In some embodiments, a short pulse can limit damage to an ITO electrode, hydrophobic layer, or inhibit bubbles created by water electrolysis.

In some embodiments, the control system can isolate or turn-off the array of electrodes for a period of between about 5 ms and about 100 ms, and the length of time a lysing signal is applied can be between about 1 ms and about 50 ms.

In some embodiments, the peak voltage of the lysing signal can be about 100 volts (e.g., 100V DC).
In some embodiments, the lysing signal can be direct current voltage.

In some embodiments, the device can have a second substrate facing the hydrophobic surface of the insulator layer and supporting at least one lysing electrode.

In some embodiments, the apparatus can be configured to: receive a droplet having a sample to be analysed; manoeuvre the droplet to lysing electrodes for lysing said sample for rupturing calls therein; manoeuvre at least a portion of the lysed droplet to a measurement electrode; move a second droplet adjacent the lysed droplet to form a droplet interface bilayer; and performing measurements on the sample using the droplet interface.

Following lysing, the apparatus can move and/or mix the lysed sample for preparation before creating a droplet interface bilayer and subsequent experiments, in some embodiments.

In some embodiments, after manoeuvring the droplet to lysing electrodes the apparatus can be further configured to collate content of the droplet in a group using dielectrophoresis such that the group of contents are arranged for lysing for rupturing cells therein.

In some embodiments, the apparatus can apply the dielectrophoresis field between the lysing electrodes. In some embodiments, the control system can be arranged to modify the at least one formed system of droplets in response to outputs of the sensor system.

In some embodiments, the outputs of the sensor system can include electrical measurements taken by the sensor system.

In some embodiments, the sensor system can further comprise an analysis system configured to process the electrical measurements, and said outputs of the sensor system can include outputs of the analysis system.

In some embodiments, the control system can be configured to apply actuation signals to the actuation electrodes selected to modify the formed system of droplets by separating a droplet interface in the system.

In some embodiments, the control system can be configured to apply actuation signals to the actuation electrodes selected to modify the formed system of droplets by moving a new droplet into contact with a current droplet in the system of droplets and forming a droplet interface between the new droplet and the current droplet.

In some embodiments, the control system can be configured to apply actuation signals to the actuation electrodes selected to modify the formed system of droplets by moving a new droplet into contact with a current droplet in the system of droplets and fusing the new droplet and the current droplet.

In some embodiments, the new droplet does not comprise amphipathic molecules at the interface between the liquid of the droplet and the fluid medium.

In some embodiments, the control system can be configured to apply actuation signals to the actuation electrodes selected to form plural systems of droplets in parallel.

In some embodiments, the control system can be configured to apply actuation signals to the actuation electrodes selected to form at least one system of droplets having one or more droplet interfaces between the droplets using a method described herein.

In some embodiments, the electrical measurements can include impedance measurements.

In some embodiments, the sensor system can be configured to take electrical measurements in a frequency range from a lower limit to an upper limit, wherein the lower limit is 1 Hz, 10 Hz or 100 Hz and the upper limit is 10 MHz, 100 KHz or 10 KHz, in any combination.

In some embodiments, the electrical measurements can be measurements of ion flow between droplets through a transmembrane pore.

In some embodiments, the sensor system can be arranged to take the electrical measurements while applying a potential difference between a respective pair of sensor electrodes.

In some embodiments, the sensor system can further comprise an analysis system configured to process the electrical measurements.

In some embodiments, the analysis system can be configured to process the electrical measurements to analyse an analyte that interacts with a transmembrane pore inserted into a formed droplet interface comprising a membrane of amphipathic molecules.

In some embodiments, the analyte can be a polymer comprising polymer units and the sensor system can be configured to process the electrical measurements to derive estimated identities of polymer units of the polymer.

In some embodiments, the apparatus can further comprise a droplet preparation system configured to form droplets disposed on the hydrophobic surface of the electro-wetting device in the fluid medium, wherein the control system is configured to control the droplet preparation system to form the droplets.

In some embodiments, the insulator layer can comprise a layer of electrically insulating material coated by a hydrophobic material that forms said hydrophobic surface.

In some embodiments, the apparatus can further comprise a second substrate facing the hydrophobic surface of the insulator layer, wherein the second substrate is coated by a hydrophobic material forming a further hydrophobic surface facing the hydrophobic surface of the insulator layer, the droplets being disposed on the further hydrophobic surface of the hydrophobic layer as well as the hydrophobic surface of the insulator layer.

In some embodiments, the sensor system can comprise sensor electrodes supported on the second substrate and that make an electrical connection with the droplets.

In some embodiments, the control system can be arranged, while applying actuation signals to the actuation electrodes, to apply a reference signal to the sensor electrodes.

In some embodiments, the EWOD device can further comprise a further electrode, and wherein the control system is arranged, while applying actuation signals to the actuation electrodes, to apply a reference signal to the further electrode.

In some embodiments, the EWOD device can further comprise an active matrix arrangement connected to the actuation electrodes.

In some embodiments, the EWOD device can be arranged to receive droplets comprising amphipathic molecules at their surface and containing a transmembrane pore and the control system can be configured to apply actuation signals to the actuation electrodes selected to form at least one system of droplets having one or more droplet interfaces comprising a membrane of amphipathic molecules between the droplets such that a transmembrane pore is allowed to insert into a formed droplet interface.

In some embodiments, the EWOD device can be arranged to receive droplets containing an analyte capable of interaction with the transmembrane pore and the sensor system is configured to take measurements that are dependent on interaction of the analyte with the transmembrane pore.

In some embodiments, the apparatus can be used in combination with a fluid medium and droplets comprising liquid in the fluid medium disposed on the hydrophobic surface of the electro-wetting device.

In some embodiments, one of the liquid and the fluid medium can be polar, and the other of the liquid and the fluid medium is apolar, the droplets further comprising amphipathic molecules at the interface between the liquid of the droplets and the fluid medium, and the droplet interfaces comprise a membrane of amphipathic molecules.

In some embodiments, the liquid can be polar, and the fluid medium is apolar.

In some embodiments, the fluid medium can be a liquid medium.

In some embodiments, at least one of the droplets can comprise a transmembrane pore that is capable of insertion into the membrane of amphipathic molecules.

In some embodiments, at least one of the droplets can comprise an analyte that is capable of interaction with the transmembrane pore.

According to a fifth aspect there is a method for preparing an analyte in an apparatus as hereinbefore described and claimed, the method comprising: contacting a first droplet containing a cell of interest with at least two actuation electrodes, said electrodes connectable to the lyser for applying a lysing signal to the first droplet to lyse said cell; connecting the lyser to an electrode pair in contact with the first droplet to lyse the cell and release analyte of interest from the cell.

According to a sixth aspect, there is a method of measuring an analyte in an apparatus as hereinbefore described and claimed, the method further comprising: bringing a second droplet in to contact with the first droplet to form a droplet pair, wherein the first droplet and second droplet contact respective measurement electrodes.

In some embodiments, the method can further comprise using dielectrophoresis to group cells within the droplet prior to lysing.

In some embodiments, the dielectrophoresis can be applied between the lysing electrodes in order to group the cells at the lysing electrodes for lysing.

In some embodiments, following lysing of the cells and release of the analyte into the droplet, a further dielectrophoresis field can be applied to the droplet to hold the analyte at the lysing electrodes.

In some embodiments, the method can further include: dividing the first droplet to form a first sub-droplet and a second sub-droplet to form a first droplet pair; bringing a second droplet in to contact with the first sub-droplet to form a second droplet pair and contacting the first sub-droplet and the second droplet with respective measurement electrodes; and bringing a third droplet in to contact with the second sub-droplet to form a second droplet pair and contacting the second sub-droplet and third second droplet with respective measurement electrodes.

In some embodiments, the method can further comprise providing an ion channel at the interface between any of the droplet pairs to provide a fluid pathway between the droplet pair.

In some embodiments, the method can further comprise the step of taking electrical measurements between any of the droplet pairs using the sensor system in order to measure a property of an analyte or detect the analyte.

In some embodiments, the analyte of interest can be a polynucleotide. In some embodiments, the ion channel can be a nanopore. In some embodiments, the electrical measurements can be taken during translocation of the polynucleotide through the nanopore. A sequence characteristic of the polynucleotide can be determined from the electrical measurements, in some embodiments.

In some embodiments, following release of the analyte from the lysed cell, the analyte can be subjected to a sample preparation in order to optimise it for detection or measurement of the property. In some embodiments, the sample preparation can be carried out by contacting the analyte with one or more sample preparation reagents.

In some embodiments, the one or more sample preparation reagents can be provided in one or more further droplets. In some embodiments, following lysing of the cell the first droplet can be moved to contact a measurement electrode.

The first to sixth aspects of the present invention may be implemented together, for example in the same device or apparatus. Accordingly, the preferred features of the first to third aspects of the present invention, some of which are defined in the dependent claims below, may be combined in any combination.

BRIEF DESCRIPTION OF THE DRAWINGS

To allow better understanding, embodiments of the present invention will now be described by way of non-limitative example with reference to the accompanying drawings, in which:

FIGS. 8 to 12 are, in accordance with certain embodiments, plan views of a pair of droplets on an array of actuation electrodes in the AM-EWOD device during successive stages of a method of forming a droplet interface between the droplets;

FIGS. 13 and 14 are, in accordance with certain embodiments, plan views of respective ways of forming two systems of three droplets;

FIGS. 15 and 16 are, in accordance with certain embodiments, plan views of respective systems of droplets.

FIGS. 17A-17B are, in accordance with certain embodiments, two images of an array of actuation electrodes in the AM-EWOD device;

FIG. 18 is, in accordance with certain embodiments, a diagram of a patterned layer of conductive material in the AM-EWOD device;

FIG. 19 is, in accordance with certain embodiments, an image of an array of actuation electrodes in the AM-EWOD device on which three systems of two droplets are formed;

FIG. 20 is, in accordance with certain embodiments, images of two sets of three droplets before and after formation of two droplet interfaces therebetween;

DETAILED DESCRIPTION

Overall Apparatus

Figure 1:
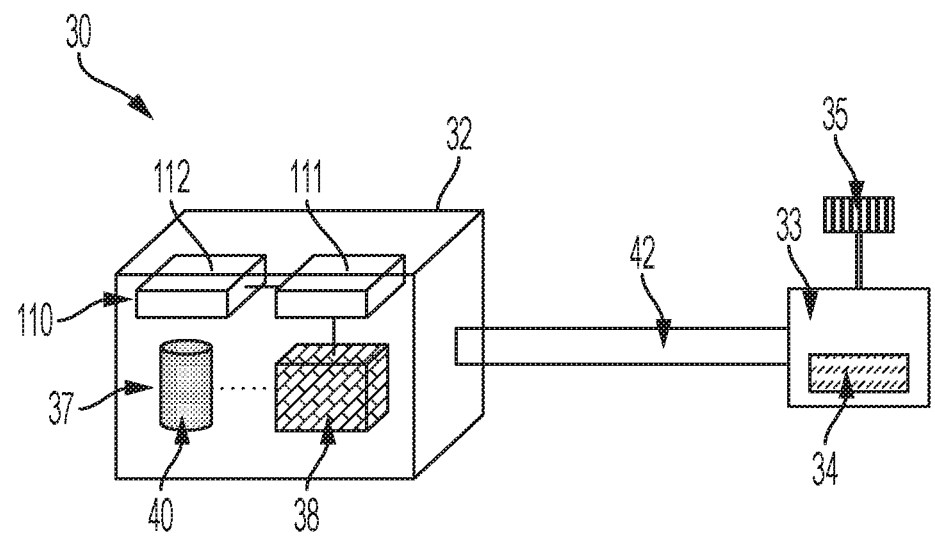
FIG. 1 is, in accordance with certain embodiments, a schematic view of an apparatus including an AM-EWOD device.
Figure 2:
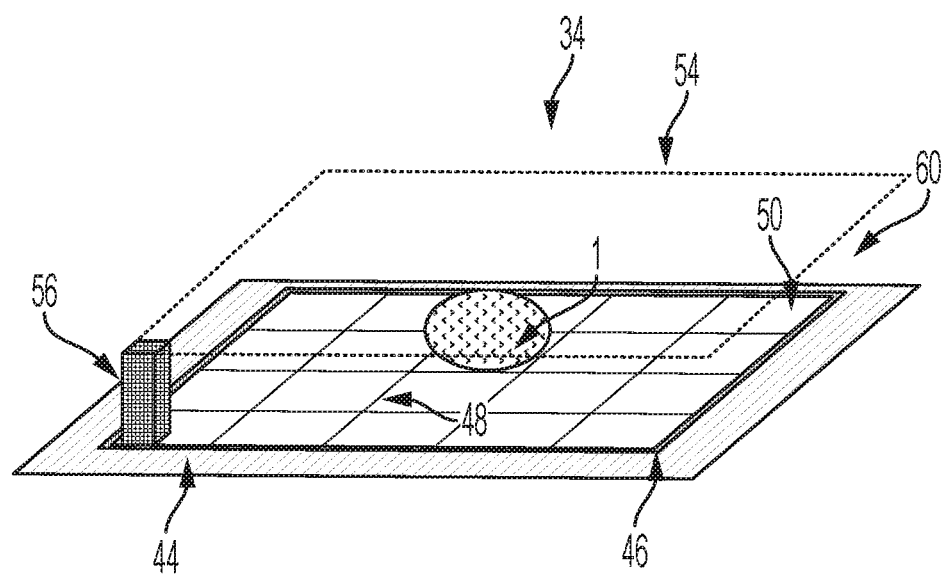
FIG. 2 is, in accordance with certain embodiments, a schematic perspective view of the AM-EWOD device.

FIG. 1 illustrates, in accordance with certain embodiments, apparatus 30 for forming droplet interfaces and for performing experiments thereon. In some embodiments, apparatus 30 includes reader 32 and cartridge 33 that may be inserted into reader 32. In some embodiments, cartridge 33 contains AM-EWOD device 34 which is an example of an electro-wetting device. AM-EWOD device 34 is shown in FIG. 2, in accordance with certain embodiments, and described further below.

In some embodiments, reader 32 and cartridge 33 may be electrically connected together while in use, for example by a cable of connecting wires 42, although various other methods (e.g. wireless connection) of providing electrical communication may be used.

In some embodiments, reader 32 also comprises droplet preparation system 35 configured to form droplets 1 comprising liquid in fluid medium 60 in AM-EWOD device 34 when cartridge 33 is inserted. Suitable material properties for droplets 1 and fluid medium 60 are discussed below. In some embodiments, droplet preparation system 35 may also be able to carry sample preparations to prepare an analyte to be measured, alternatively sample preparation may be carried out in AM-EWOD device 34. In some embodiments, the samples may be compartmentalised for a library preparation or for sequencing.

In some embodiments, the droplet preparation system 35 may comprise fluid input ports that perform the function of inputting liquid into AM-EWOD device 34 from one or more reservoirs and thereby generating droplets within AM-EWOD device 34. In some embodiments, droplet preparation system 35 may be formed by conventional fluidics elements, for example controlling flow of liquid by electro-wetting. In some embodiments, droplet preparation system 35 desirably has the ability to accurately control the volumes of created droplets 1, accurate to 2-3%, in some embodiments. In some embodiments, the droplets may have respective volumes between 1 nL and 10 µL.

In some embodiments, apparatus 30 further includes control system 37 provided in reader 32. In this example, control system 37 includes control electronics 38 and storage device 40 that may store any application software any data associated with the system. In some embodiments, control electronics 38 may include suitable circuitry and/or processing devices that are configured to carry out various control operations relating to control of AM-EWOD device 34, such as a CPU, microcontroller or microprocessor.

Among their functions, to implement the features of the present invention, control electronics 38 may comprise a part of overall control system 37 that may execute program code embodied as a control application within storage device 40, in some embodiments. In some embodiments, the storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof.

As described in more detail below, in some embodiments, control system 37 is configured to perform control of various elements of the apparatus, including control of droplet preparation system 35, to form droplets 1 and control of the application of actuation signals for manipulating droplets. In particular, in some embodiments, control system 37 is configured to form one or more systems of two or more droplets 1. In some embodiments, within the or each system of droplets 1, one or more droplet interfaces are formed between respective pairs of droplets 1. In some embodiments, control system 37 may also provide a graphical user interface (GUI) to a user which provides for the user to input program commands such as droplet operations (e.g. move a droplet), assay operations (e.g. perform an assay), and for displaying the results of such operations to the user. As described below, in some embodiments, control system 37 can additionally manage preparation system 35 to lyse cells.

Electro-Wetting Device

Figure 3:
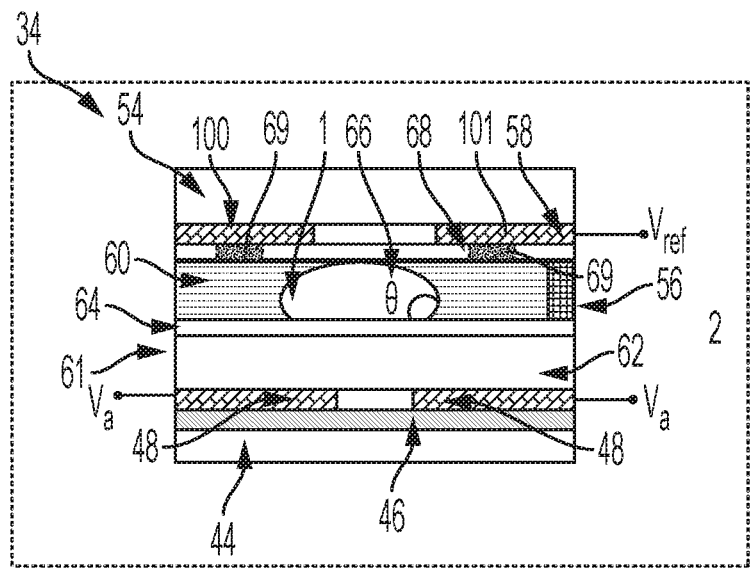
FIG. 3 is, in accordance with certain embodiments, a cross-sectional side view of a portion of the AM-EWOD device.

FIGS. 2 and 3 illustrate, in accordance with certain embodiments, AM-EWOD device 34.

As seen in FIG. 2, AM-EWOD device 34 has first substrate 44 (which is the lowermost substrate in FIGS. 2 and 3) with thin film electronics 46 disposed upon first substrate 44, in some embodiments. In some embodiments, array 50 of electrodes 48 (e.g., actuation electrodes) are supported by first substrate 44 on top of thin film electronics 46. In some embodiments, thin film electronics 46 are arranged to drive electrodes 48 (e.g., actuation electrodes).

In some embodiments, array 50 of electrodes 48 (e.g., actuation electrodes) may be an X by Y rectangular array, where X and Y are any integers. In some embodiments, electrodes 48 (e.g., actuation electrodes) may be formed, for example, from indium tin oxide (ITO) or another transparent metal oxide, or a metal, or any other electrically conductive material. In some embodiments, AM-EWOD device 34 has a first substrate and also includes second substrate 54 (which is the uppermost substrate in FIGS. 2 and 3) separated by spacer 56 from first substrate 44. As described further below, in some embodiments, droplets 1 are disposed between first substrate 44 and second substrate 54. A single droplet is shown in FIGS. 2 and 3 but multiple droplets 1 are present, in some embodiments.

The layered structure of AM-EWOD device 34 is best seen in FIG. 3 which illustrates, in accordance with certain embodiments, a portion thereof including two electrodes 48 (e.g., actuation electrodes) supported by first substrate 44. In some embodiments, electrodes 48 (e.g., actuation electrodes) may be formed from a patterned layer of conductive material.

In some embodiments, insulator layer 61 comprising layer 62 of electrically insulating material coated by hydrophobic material 64 is disposed on first substrate 44, covering electrodes 48 (e.g., actuation electrodes). In some embodiments, hydrophobic material 64 forms an outermost hydrophobic surface of insulator layer 61.

In some embodiments, second substrate 54 faces the hydrophobic surface of insulator layer 61. In some embodiments, second substrate 54 supports layer 58 of conductive material that is deposited on the surface of second substrate 54 facing insulator layer 61. In some embodiments, layer 58 of conductive material is patterned to form more electrodes, as described in more detail herein.

In some embodiments, second substrate 54 is coated by hydrophobic material 68 that covers layer 58 of conductive material and forms a further hydrophobic surface facing the hydrophobic surface of insulator layer 61.

In some embodiments, hydrophobic materials 64 and 68 may be formed by any suitable materials (which may be the same or different), for example a fluoropolymer.

In some embodiments, droplets 1 are received in AM-EWOD device 34, disposed within fluid medium 60. In some embodiments, droplets 1 and fluid medium 60 are disposed on the hydrophobic surface of insulator layer 61 and on the further hydrophobic surface of hydrophobic material 68 that coats second substrate 54. In this manner, droplets 1 are sandwiched between first and second substrates 44 and 54, which constrain the shape of the droplets 1, in some embodiments. In some embodiments, this improves the degree of control of droplets 1 by the actuation signals applied to electrodes 48 (e.g., actuation electrodes) in the manner described below.

In some embodiments, droplets 1 have contact angle 66 with the hydrophobic surface of insulator layer 61. Contact angle 66 is determined by the balancing of the surface tension components (1) from the hydrophobic surface to the liquid of the droplets 1 ($\Gamma_{SL}$) interface, (2) from the liquid of the droplets 1 to the surrounding fluid medium 60 ($\Gamma_{LG}$) interface, and (3) from the hydrophobic surface to the surrounding fluid medium 60 ($\Gamma_{SG}$) interface. Where no voltages are applied, contact angle 66 satisfies Young's law, and is of size θ given by the equation $\cos θ=((\Gamma_{SG}-\Gamma_{SL})/\Gamma_{LG})$.

Accordingly, in some embodiments, electrodes 48 (e.g., actuation electrodes) are capable of electro-wetting droplets 1 when actuation signals are applied to electrodes 48 (e.g., actuation electrodes). In some embodiments, actuation signals create electrical forces that effectively control the hydrophobicity of the hydrophobic surface of insulating layer 61, and thereby energise droplet 1. In some embodiments, in such an energised state, droplets 1 will have a shape that is modified compared to when droplets 1 are in a lower energy state, i.e. a state in which the actuation signals provide less or no energy to droplets 1.

Such references to the shape being modified may refer to the shape in the plane of AM-EWOD device 34, i.e. parallel to the hydrophobic surface of insulator layer 61. In some embodiments, although energy supplied by the actuation signals will modify the three-dimensional shape of droplets 1, the shape is most greatly affected in the plane of AM-EWOD device 34, being the direction in which electrodes 48 (e.g., actuation electrodes) are arrayed.

Similarly, references to the shape being modified compared to when in a lower energy state may refer to the shape of the contact line of droplets 1. In this context, the term "contact line" has its normal meaning of the line along which the interface between droplet 1 and fluid medium 60 contacts the hydrophobic surface of insulating layer 61 above electrodes 48 (e.g., actuation electrodes).

In some embodiments, by selective control of the pattern of actuation signals applied to selected electrodes 48 (e.g., actuation electrodes), droplets 1 may be manipulated and moved in the lateral plane between first and second substrates 44 and 54. In general terms, such manipulation of droplets 1 in this manner may apply techniques known for EWOD devices, in some embodiments.

In some embodiments, actuation signals may take any form suitable for electro-wetting droplets 1. In some embodiments, the actuation signals may be AC actuation signals, but they could also be DC voltage potentials with respect to a reference voltage. In some embodiments, while applying the actuation signals, a reference signal is applied to reference electrode 59 elsewhere in the AM-EWOD device, as described further below.

In some embodiments, the reference signal may take any suitable form. In one example, the reference signal may be a fixed reference voltage. In another example where the actuation signals are AC actuation signals, the reference signal may be an AC reference signal which is in anti-phase with the AC actuation signals. In this example, the magnitude of the potential difference between electrodes 48 (e.g., actuation electrodes) and reference electrode 59 is increased, for example being doubled when the AC actuation signals and the AC reference signal are of equal magnitude, compared to a reference signal that is a fixed reference voltage.

Figures 4A, 4B:
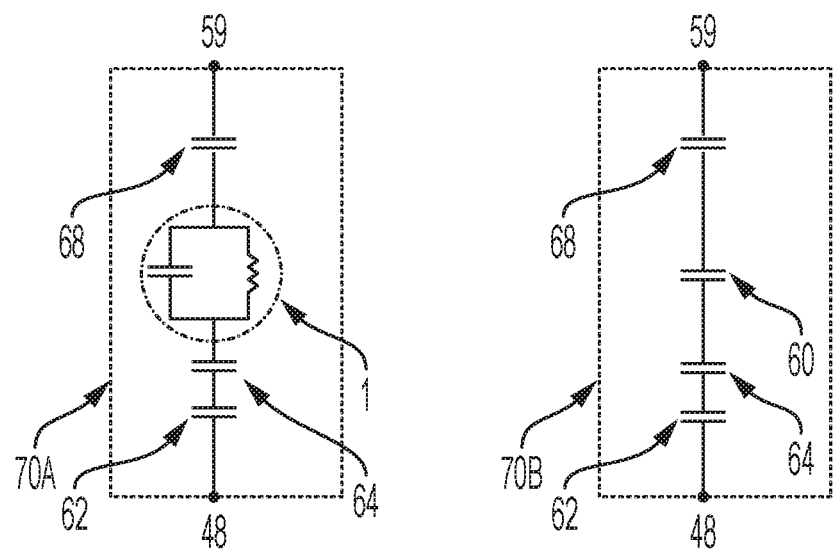
FIGS. 4A and 4B are, in accordance with certain embodiments, diagrams of a circuit representation of the electrical load presented at the actuation electrode when a liquid droplet is present and not present, respectively.

FIG. 4A shows, in accordance with certain embodiments, a simplified circuit representation of electrical load 70A between electrode 48 (e.g., actuation electrode) and reference electrode 59 in the case where droplet 1 is present. In some embodiments, droplet 1 can be modelled as a resistor and capacitor in parallel. In some embodiments, the resistance of droplet 1 will be relatively low (e.g. if the droplet contains ions) and the capacitance of the droplet will be relatively high (e.g. because the relative permittivity of polar liquids is relatively high, e.g. ~80 if droplet 1 is aqueous). In many situations, the droplet resistance is relatively small, such that at the frequencies of interest for electro-wetting, droplet 1 may function effectively as an electrical short circuit. In some embodiments, hydrophobic materials 64 and 68 have electrical characteristics that may be modelled as capacitors, and the insulating material of layer 62 may also be modelled as a capacitor. In some embodiments, the overall impedance between electrode 48 (e.g., actuation electrode) and reference electrode 59 may be approximated by a capacitor whose value is typically dominated by the contribution of the insulating material of layer 62 and hydrophobic materials 64 and 68 contributions, and which for typical layer thicknesses and materials may be on the order of a pico-Farad in value.

FIG. 4B shows, in accordance with certain embodiments, a circuit representation of electrical load 70B between electrode 48 (e.g., actuation electrode) and reference electrode 59 in the case where no droplet 1 is present. In this case, the droplet components are replaced by a capacitor representing the capacitance of fluid medium 60 (e.g., non-polar fluid) which occupies the space between the top and first substrates. In this case, the overall impedance between electrode 48 (e.g., actuation electrode) and reference electrode 59 may be approximated by a capacitor whose value is dominated by the capacitance of the non-polar fluid and which is typically small, of the order of femto-Farads.

For the purposes of driving and sensing electrodes 48 (e.g., actuation electrodes), electrical loads 70A and 70B overall function in effect as a capacitor, whose value depends on whether droplet 1 is present or not at a given electrode 48 (e.g., actuation electrode), in some embodiments. In some embodiments, where a droplet is present, the capacitance is relatively high (typically of order pico-Farads), whereas if there is no droplet 1 present the capacitance is low (typically of order femto-Farads). In some embodiments, if a droplet partially covers a given electrode 48 then the capacitance may approximately represent the extent of coverage of electrode 48 (e.g., actuation electrode) by droplet 1.

Figure 5:
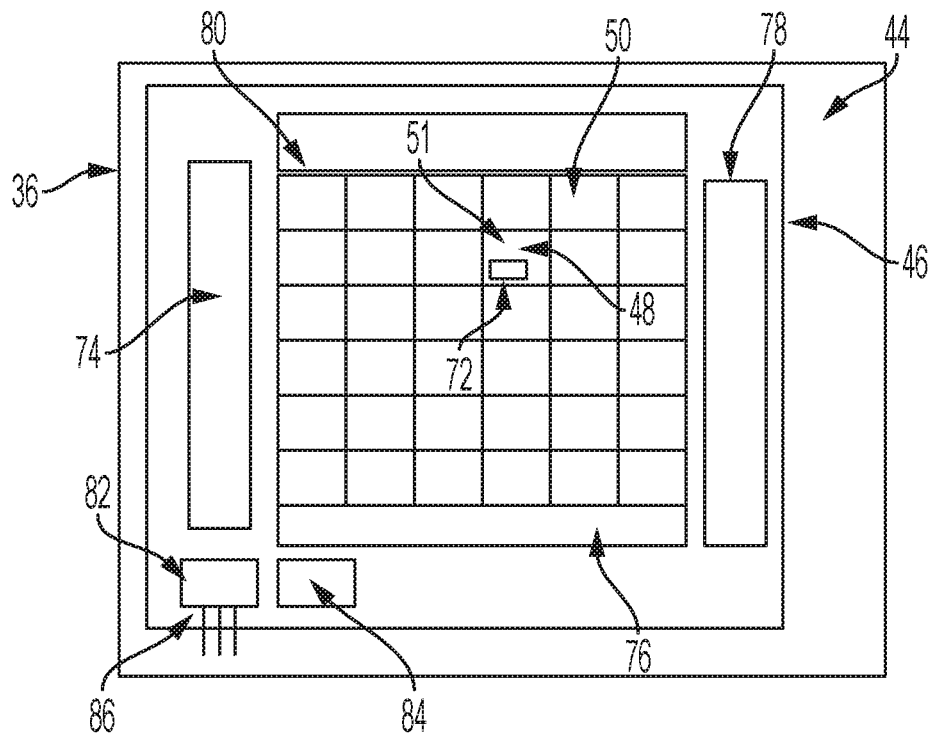
FIG. 5 is, in accordance with certain embodiments, a plan view of thin film electronics in the AM-EWOD device.

FIG. 5 illustrates, in accordance with certain embodiments, the arrangement of thin film electronics 46 in AM-EWOD device 34. In some embodiments, thin film electronics 46 is located on first substrate 44 and comprises an active matrix arrangement of array elements 51 each comprising array element circuit 72 for controlling the electrode potential of a corresponding electrode 48 (e.g., actuation electrode). In some embodiments, integrated row driver 74 and column driver 76 circuits are also implemented in thin film electronics 46 to supply control signals to array element circuit 72. In this manner, in some embodiments, array element circuit 72 may perform a function of selectively, under the control of control system 37, actuating electrode 48 (e.g., actuation electrode) to applying an actuation signal to electrode 48 (e.g., actuation electrode). Thus, in some embodiments, control system 37 controls the actuation signals applied to electrodes 48 (e.g., actuation electrodes), such as required voltage and timing signals to perform droplet manipulation operations.

Figure 6:
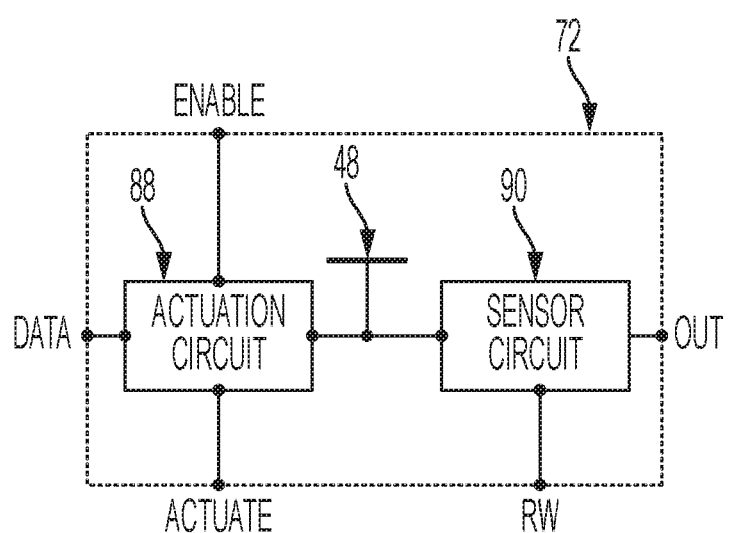
FIG. 6 is, in accordance with certain embodiments, a diagram of an array element circuit of the AM-EWOD device.

FIG. 6 illustrates, in accordance with certain embodiments, the arrangement of array element circuit 72 present in each array element 51. In some embodiments, array element circuit 72 contains actuation circuit 88, having inputs ENABLE, DATA and ACTUATE, and an output which is connected to electrode 48 (e.g., actuation electrode).

In some embodiments, serial interface 82 may also be provided to process a serial input data stream and facilitate the programming of the required voltages to electrodes 48 (e.g., actuation electrodes) in array 50. In some embodiments, voltage supply interface 84 provides the corresponding supply voltages, second substrate drive voltages, and other requisite voltage inputs. In some embodiments, a number of connecting wires 86 between first substrate 44 and external control electronics, power supplies and any other components can be made relatively few, even for large array sizes. Optionally, the serial data input may be partially parallelized. For example, in some embodiments, if two data input lines are used, the first may supply data for columns 1 to X/2, and the second for columns (1+X/2) to M with minor modifications to column driver circuits 76. In this way the rate at which data can be programmed to array elements 51 is increased, in some embodiments, which is a standard technique used in Liquid Crystal Display driving circuitry.

Droplet Interface Sensing

Figure 7:
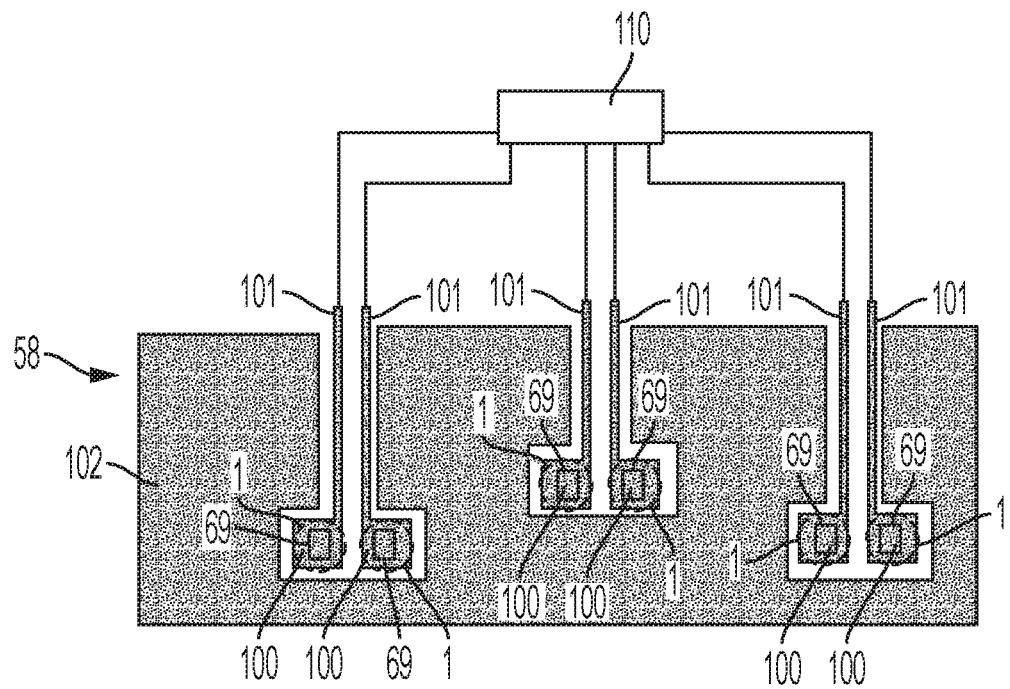
FIG. 7 is, in accordance with certain embodiments, a plan view of a layer of conductive material formed on a second substrate of the AM-EWOD device.

FIG. 7 shows, in accordance with certain embodiments, how layer 58 of conductive material is patterned to form sensor electrodes 100, conductive tracks 101, and further electrodes 102 which are therefore deposited on second substrate 54 and supported thereby.

In some embodiments, sensor electrodes 100 are arranged to make an electrical connection with respective droplets 1. In some embodiments, the provision of sensor electrodes 100 is a convenient and reliable way to make electrical connections to droplets 1, for example to take electrical measurements between droplets 1 across a droplet interface formed therebetween. In contrast, in some embodiments, such a type of electrical connection is not possible from electrodes 48 (e.g., actuation electrodes) due to the presence of insulating layer 61 including layer 62 of electrically insulating material between electrodes 48 (e.g., actuation electrodes) and droplets 1.

In some embodiments, hydrophobic material 68 that covers layer 58 of conductive material coating second substrate 54 is provided with apertures 69 that expose part of sensor electrodes 100, although more generally the apertures may be larger and expose the entirety of sensor electrodes 100. In some embodiments, apertures 69 in hydrophobic material 68 assist in making an electrical contact between sensor electrodes 100 and droplets 1. In some embodiments, fluid medium 60 and/or the liquid of droplets 1 can flow into apertures 69, and have a lower electrical impedance than hydrophobic material 68, thereby providing a conductive path.

In some embodiments, apertures 69 may have the additional advantage of acting as a hydrophilic patch which helps to pin droplets 1 in position if the electrodes are de-actuated or the device is de-powered.

In some embodiments, apertures 69 may be created by selective removal of hydrophobic material 68, for example by means of a dry etch process or lift off process.

However, in some embodiments, apertures 69 are not essential and instead an electrical connection between sensor electrodes 100 and droplets 1 can be made through hydrophobic material 68, which may be of sufficiently low impedance (either real or imaginary parts) that an electrical measurement can still be taken through it. In that case, the thickness and material properties of hydrophobic material 68 are chosen accordingly.

In some embodiments, sensor electrodes 100 are arranged in sets and sensor electrodes 100 of each set are sized and shaped to make an electrical connection with droplets 1 between which a droplet interface is formed in a respective system of droplets 1. In some embodiments, this may be achieved by the area of sensor electrodes 100 being similar to the area enclosed by the contact line of droplets 1 with sensor electrodes 100, and distance between the centre of sensor electrodes 100 within each set and being similar to the distance between the centre of droplets 1 in the formed system. In some embodiments, each set of sensor electrodes 100 may be aligned with a respective system of droplets 1 for making electrical connections to respective droplets 1 in that system of droplets 1. Thus, in some embodiments, control system 37 may be configured to form plural systems of two or more droplets 1, where each system of droplets 1 is aligned with a respective set of sensor electrodes 100.

By way of illustration, FIG. 7 shows, in accordance with certain embodiments, three sets of two sensor electrodes 100 and three systems of two droplets 1 formed in alignment with sensor electrodes 100 of the respective sets. However, in some embodiments, there could be any number of sets of sensor electrodes 100, and the sets could contain any number of sensor electrodes 100 in dependence in the number of droplets 1 to be included in each system.

In some embodiments, as a result of this configuration, systems of droplets 1 may be formed in parallel and experiments may be performed thereon in parallel using the respective sets of sensor electrodes 100. In some embodiments, any number of systems of droplets 1 may be formed, for example two or more, up to large numbers of order tens of thousands.

In some embodiments, conductive tracks 101 are connected to sensor electrodes 100 and extend to the edge of layer 58 of conductive material where an electrical connection is made to a droplet interface sensor system 110 described further below. Thus, in some embodiments, conductive tracks 101 provide an electrical connection from sensor electrodes 100 to droplet interface sensor system 110.

In some embodiments, further electrode 102 extends around sensor electrodes 100 and conductive tracks 101.

In some embodiments, further electrode 102 may function as reference electrode 59 in the circuit representations shown in FIGS. 4A and 4B. In that case, control system 37 is connected to further electrode 102 and is arranged to apply a reference signal to further electrode 102, while applying actuation signals to electrodes 48 (e.g., actuation electrodes).

However, in some embodiments, further electrode 102 is not essential. In some embodiments, when further electrode 102 is absent, or even when further electrode 102 is present, a different electrode(s) may function as reference electrode 59. In one example, sensor electrodes 100 may function as reference electrode 59.

In another example, reference electrode 59 may be provided elsewhere between first and second substrates 44 and 54, for example as a separate element such as an in-plane reference electrode. In any such example, control system 37 is connected to reference electrode 59, e.g. the sensor electrodes 100, and is arranged to apply a reference signal to reference electrode 59, while applying actuation signals to electrodes 48 (e.g., actuation electrodes), in some embodiments. In such an arrangement, in some embodiments, unactuated electrodes 48 (e.g., actuation electrodes) on first substrate 44 may operate as a reference and droplets 1 can be moved without needing a reference electrode on the second substrate 54.

In some embodiments, reader 32 further comprises droplet interface sensor system 110 including measurement unit 111 which is connected to sensor electrodes 110 and takes electrical measurements between sensor electrodes 110 that are electrically connected to respective droplets 1, across droplet interfaces formed therebetween. In some embodiments, measurement unit 111 is controlled to take electrical measurements out while actuation signals are not applied to electrodes 48 (e.g., actuation electrodes). In some embodiments, this has the advantage of reducing the risk of the actuation signals affecting the electrical measurements, for example by physically affecting or damaging the system of droplets being measured or by causing electrical interference with measurement unit 111.

In some embodiments, the elements of thin film electronics 46 are electrically isolated from sensor electrodes 100 and measurement unit 111, so do not participate in taking of the electrical measurements.

Any suitable electrical measurements may be taken, for example impedance, current or capacitance measurements. In a possible configuration, the electrical measurements may be taken by applying a voltage and measuring the current sourced through one of sensor electrodes 100, whilst the other sensor electrode is grounded. In some embodiments, the real and imaginary parts of the electrical impedance of the droplet interface 2 may thus be determined.

In some embodiments, measurement unit 111 may be formed by suitable electronic components suitable for droplet interface experiments, for example including detection channels including amplifier arrangements. In one example, measurement unit 111 may comprise a patch clamp arrangement. In another example, measurement unit 111 may have the same construction as the signal processing function described in WO-2011/067559. In some embodiments, the electrical measurements may be taken in a frequency range from a lower limit to an upper limit, wherein the lower limit is 1 Hz, 10 Hz or 100 Hz and the upper limit is 10 MHz, 100 KHz or 10 KHz, in any combination.

In some embodiments, the measurement unit 111 may be arranged to apply a potential difference between a respective pair of sensor electrodes 100 across which measurements are taken, while taking those measurements.

In some embodiments, measurement unit 111 is controlled by control system 37 to take electrical measurements from any of the systems of droplets 1 after they have been formed in AM-EWOD device 34 under the control of control system 37.

The electrical measurements may be of any suitable type, for example being impedance measurements and/or measurements of ion current flow across the droplet interface. In some embodiments, where the measurements are taken across droplet interface comprising a membrane of amphipathic molecules having a transmembrane pore inserted therein, the electrical measurements may be, for example, measurements of ion current flow between the droplets through the transmembrane pore and/or electrical measurements that are dependent on an analyte that interacts with the transmembrane pore.

In some embodiments, the measurements may be optical or a combination of optical and electrical, such as disclosed by Soni G V et al., Rev Sci Instrum. 2010 January; 81(1): 014301 and T Gilboa and A Meller, Analyst, 2015, 140, 4733-4747.

In some embodiments, droplet interface sensor system 110 may further comprise an analysis system 112 configured to process the electrical measurements that are dependent on an analyte that interacts with a transmembrane pore, in order to analyse the analyte. For example, where the analyte is a polymer comprising polymer units, the analysis system may be configured to process the electrical measurements to derive estimated identities of the polymer units of the polymer. In some embodiments, analysis system 112 may process the electrical measurements using any suitable known technique, some examples of which are described further below.

In some embodiments, analysis system 112 may be formed by an appropriate combination of (1) a hardware stage, for example a field programmable gate array (FPGA), to pre-process the electrical measurements supplied as a signal from the measurement unit 111, and (2) a processor for processing the signals supplied from the hardware stage. In some embodiments, the processor may be any suitable form of processing device. In some embodiments, the processor may be implemented within reader 32 as shown in FIG. 1, and may execute software which may be stored in storage device 40. As an alternative, in some embodiments, the processor could be implemented by a processing device, for example a conventional computer apparatus, external to reader 32.

By way of example, measurement unit 111 and analysis system 112 may have the same construction as the signal processing function described in WO-2011/067559.

In some embodiments, droplet interface sensor system 110 may be combined with other types of measurement system to take measurements, for example capacitance measurements from the actuation electrodes, measurements from additional electrodes (not shown) and/or measurements using electro-magnetic radiation, including but not limited to absorbance or emission infrared, ultraviolet, which techniques may employ labelled dyes or antibodies, and/or fluorescence resonance energy transfer (FRET).

Droplet Sensing

In some embodiments, array element circuit 72 also may contain a droplet sensor circuit 90, which is in electrical communication with electrode 48 (e.g., actuation electrode). In some embodiments, droplet sensor circuit 90 provides a sensing capability for detecting the presence or absence of droplet 1 in the location of each electrode 48 (e.g., actuation electrode). In this manner, in some embodiments, array element circuit 72 may also perform a function of sensing the presence or absence of droplet 1 at the location of array element 51 during manipulation of droplets 1. However, due to the presence of insulating layer 61 including layer 62 of electrically insulating material between electrodes 48 (e.g., actuation electrodes) and droplets 1, it may be difficult or inconvenient to take electrical measurements suitable for studying a droplet interface or processes occurring at a droplet interface, in some embodiments.

In some embodiments, droplet sensor circuit 90 may conveniently employ capacitive sensing using an impedance sensor circuit. In some embodiments, droplet sensor circuit 90 may include impedance sensor circuitry of the type known in the art, as described for example in U.S. Pat. No. 8,653,832 and GB-2,533,952. As described therein, droplets 1 may be actuated by means of electro-wetting and may be sensed by capacitive or impedance sensing means, in some embodiments. In some embodiments, capacitive and impedance sensing may be analogue and may be performed simultaneously, or near simultaneously, at every array element 51. In some embodiments, by processing the returned information from such a sensor (for example in the application software in storage device 40 of reader 32), control system 37 can determine in real-time, or almost real-time the position, size, centroid and perimeter of each droplet 1 present in the AM-EWOD device.

Alternatively, in some embodiments, such sensing may be performed by some other means, for example optical or thermal means. In some embodiments, an alternative to droplet sensor circuit 90 is to provide an external sensor such as an optical sensor that can be used to sense droplet properties, as is known in the field of electro-wetting devices.

In some embodiments, control system 37 generates and outputs control signals for droplet sensor circuit 90 to perform sensing operations during manipulation of droplets 1. In some embodiments, integrated sensor row addressing 78 and column detection circuits 80 are implemented in thin film electronics 46 for the addressing and readout of droplet sensor circuit 90 in each array element circuit 72. In some embodiments, the read-out of droplet sensor circuit 90 may be controlled by one or more addressing lines (e.g. RW) that may be common to array elements 51 in the same row of array 50, and may also have one or more outputs, e.g. OUT, which may be common to all array elements 50 in the same column of array 50.

In some embodiments, control system 37 may use the output of droplet sensor circuit 90 to control the timing of the application of actuation signals to electrodes 48 (e.g., actuation electrodes) when manipulating droplets 1.

Formation of Droplet Interfaces

In some embodiments, control system 37 is configured to control AM-EWOD device 34 to form systems of droplets 1 having one or more droplet interfaces 2 between pairs of droplets 1 as follows.

Firstly, in some embodiments, control system 37 controls droplet preparation system 35 to form droplets 1 in AM-EWOD device 34, as needed for respective systems of droplets 1. In some embodiments, droplets 1 may be prepared from any appropriate reagents, as required for the experiments being performed. Suitable reagents are described below.

Next, in some embodiments, control system 37 controls the application of actuation signals to electrodes 48 (e.g., actuation electrodes) to form the systems of droplets 1.

It has been considered to simply apply actuation signals to manipulate the droplets 1 by simply moving the droplets across array 50 of electrodes 48 (e.g., actuation electrodes) from where they are formed towards each other and into contact. However, in that case, droplets 1 have a tendency to fuse and it is difficult to maintain the droplet interface between droplets 1. Optimising of conditions to promote formation of droplet interface 2 is difficult as electro-wetting is dependent on several factors which are likely to change between samples, such as salt concentration, droplet reagents (especially membrane components) and droplet size.

Accordingly, in some embodiments, a different method is implemented employing two stages, as will now be described.

An example of the method is shown in FIGS. 8 to 12 which show a plan view of a pair of droplets 1 on array 50 of electrodes 48 (e.g., actuation electrodes) successively as the droplets are manipulated during the method. In particular, FIGS. 8 to 12 show, in accordance with certain embodiments, the contact lines of the droplets on array 50 of electrodes 48 (e.g., actuation electrodes). FIGS. 8 to 12 also show, in accordance with certain embodiments, pattern 53 of actuation signals applied, by hashing of the selected electrodes 48 (e.g., actuation electrodes) to which actuation signals are applied 53. This example is merely for illustration and is not limitative. In some embodiments, various changes may be made, for example to the size of droplets 1 and the pattern of actuation signals may be made. It is also noted that FIGS. 8 to 12 relate to an example in which the liquid of droplets 1 is polar and fluid medium 60 is apolar, with the result that electrodes 48 (e.g., actuation electrodes) to which actuation signals are applied are electro-wet. In a notional alternative in which the liquid of droplets 1 is apolar and fluid medium 60 is polar, then the pattern of actuation signals would be inverted with the result that electrodes 48 (e.g., actuation electrodes) to which actuation signals are not applied attract the apolar droplets.

By way of background, it is noted that, in some embodiments, in a relaxed state of droplets 1 where they are not electro-wet by the application of actuation signals to electrodes 48 (e.g., actuation electrodes), droplets 1 would take the shape of lowest surface energy, which would generally be a circular shape where the hydrophobic surface of insulator layer 61 has uniform properties.

In a first stage of an embodiment of the method, actuation signals are applied to the selected electrodes 48 (e.g., actuation electrodes) to energise the one, or preferably both, of two droplets 1 between which a droplet interface is to be formed. For clarity of description, the case of energising both of the two droplets 1 will now be described.

In some embodiments, in the energised state, the shape of droplets 1 is modified compared to a shape of droplets 1 in the lower energy state of droplets 1. In some embodiments, in such an energised state, the two droplets 1 are moved into proximity with a gap 3 therebetween. Due to the gap 3, droplets 1 do not contact each other at this time, in some embodiments.

In some embodiments, the first stage of the method may be performed under feedback control from the droplet sensor circuit 90.

Figures 8, 9:
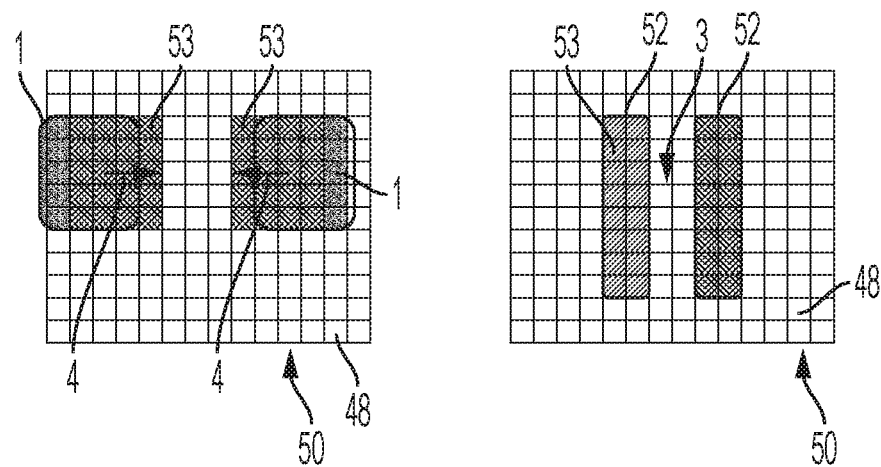

Examples of the processes applied in an embodiment of the first stage are shown in FIGS. 8 to 10, as follows.

FIG. 8 shows, in accordance with certain embodiments, a step where pattern 53 of actuation signals is applied to a square 4-by-4 group of electrodes 48 (e.g., actuation electrodes). In some embodiments, this energises the two droplets 1 to form a corresponding shape that is generally also square but with some rounding of the corners that minimises the surface energy of droplets 1. FIG. 8 also shows, in accordance with certain embodiments, how droplets 1 may be moved together. In particular, FIG. 8 shows, in accordance with certain embodiments, the case that pattern 53 of actuation signals is applied to a group of electrodes 48 (e.g., actuation electrodes) that is shifted relative to the previous step. In some embodiments, this has the result of moving droplets 1 towards the group of electrodes 48 (e.g., actuation electrodes), in the direction of arrows 4. In this manner, the droplets 1 may be shaped and may be moved, in some embodiments.

FIG. 9 shows, in accordance with certain embodiments, a step where pattern 53 of actuation signals is applied to a rectangular 2-by-8 group of electrodes 48 (e.g., actuation electrodes). In some embodiments, this energises the two droplets 1 to form a corresponding shape that is generally also rectangular but with some rounding of the corners that minimises the surface energy of droplets 1. In this step, the rectangular 2-by-8 groups of electrodes 48 (e.g., actuation electrodes), and hence droplets 1, are in proximity with a gap 3 of two columns of electrodes 48 (e.g., actuation electrodes), in some embodiments.

FIG. 10 shows, in accordance with certain embodiments, a step subsequent to that shown in FIG. 9 where the actuation signals have the same pattern 53 except that one of the 2-by-8 groups of electrodes 48 (e.g., actuation electrodes) is shifted by one column of electrodes 48 (e.g., actuation electrodes), so that the rectangular 2-by-8 groups of electrodes 48 (e.g., actuation electrodes), and hence droplets 1, are in proximity with a gap 3 of a single column of electrodes 48 (e.g., actuation electrodes). In this example, this is the final step of the first stage of the method.

In some embodiments, in a second stage of the method, the applied actuation signals are changed such that the energy of droplets 1 is lowered into a lower energy state.

In some embodiments, in this stage, the change is preferably to apply no actuation signals to electrodes 48 (e.g., actuation electrodes) that affect droplets 1. In that case, in some embodiments, no energy is supplied to droplets 1 from electrodes 48 (e.g., actuation electrodes), so the lower energy state is a state of minimum energy of droplets 1 where their shape after relaxation is affected solely by the material properties. Alternatively, in some embodiments, the change may in principle be to apply actuation signals that energise droplets 1 but to a lesser degree, so that droplets 1 relax and their shape changes but to a lesser degree than when no actuation signals are applied to electrodes 48 (e.g., actuation electrodes) that affect droplets 1.

In some embodiments, as a result of being placed in a lower energy state, the surfaces of droplets 1 that face one another across gap 3 relax into gap 3 and contact each other, thereby forming droplet interface 2 between two droplets 1. Thus, in some embodiments, the movement of the surface of droplets 1 is caused by relaxation from the energised state of droplets 1 generated in the first stage. In some embodiments, this is a passive process that provides reliable formation of droplet interface 2. In some embodiments, the rate to which droplet 1 relaxes may be dependent upon one or more factors, such as relative viscosity of the liquid of droplet 1 to that of fluid medium 60, the size of droplet 1 and/or the size of gap 3.

In some embodiments, the device geometry (size of droplets 1, height of gap between the hydrophobic surfaces, etc.) and surface tensions at droplet interfaces 2, which are themselves dependent on choice of materials and material properties, are arranged such that when the surfaces of droplets 1 touch, droplets 1 do not fuse or coalesce, but rather droplet interface 2 is formed. The geometry of the patterns of actuation signals and spatial dimensions of droplets 1 will be arranged such that droplet interface 2 is formed with a minimal surface area.

In some embodiments, the applied actuation signals may be changed in any manner to de-energise droplets 1. In some embodiments, where the actuation signals that are applied to electro-wet the actuation electrodes are AC actuation signals, then the change is desirably to replace the AC actuation signals which energised the droplets 1 by DC potentials, for example a ground potential, or by floating potentials. In some embodiments, this has the benefit that AC signals are no longer applied to the actuation signals, which assists in forming of droplet interface 2 because the presence of AC electric fields resulting from AC signals increases the risk of droplet interface 2 rupturing and causing droplets 1 to fuse when the surfaces of droplets 1 come into contact.

In some embodiments, other changes which de-energise droplets 1 may alternatively be made. In some embodiments, an alternative is to remove all power from array 50 of electrodes 48 (e.g., actuation electrodes). However, in some embodiments, it may be preferable to apply a DC potential to assist in shielding droplet interface 2 from unwanted environmental electro-magnetic interference.

The present inventors have appreciated that it is preferable, in some embodiments, not to de-actuate the droplets in the conventional way by applying AC voltage waveforms, since resultant perturbations may damage a droplet interface 2 or may interfere with electrical measurements through the droplet interface 2.

Examples of the processes applied in an embodiment of the second stage are shown in FIGS. 11 and 12, as follows.

FIG. 11 shows, in accordance with certain embodiments, a step where the pattern of actuation signals is changed compared to that shown in FIG. 10 by ceasing the application of actuation signals to the two 2-by-8 groups of electrodes 48 (e.g., actuation electrodes) and instead applying a DC potential or floating potential. FIG. 11 shows, in accordance with certain embodiments, droplets 1 at the moment where the change is made, when the droplets instantaneously have the same generally rectangular shape as before. However, in some embodiments, the droplets then relax into the lower energy state shown in FIG. 12. In some embodiments, in the absence of the other droplet 1, each droplet 1 would take its own lower energy state which is generally circular, but the centre of mass of the droplets 1 remains in generally the same location. Thus, in some embodiments, in relaxing towards those lower energy states, the surfaces of droplets 1 that face one another across gap 3 relax into gap 3 and contact each other, thereby forming droplet interface 2.

In some embodiments, the particular shapes of droplets 1 in the energised state shown in FIGS. 8 to 10 are not limitative, and in general any shape could be used that allows relaxation of droplets 1 into contact to form a droplet interface. In some embodiments, the shape of the energised contact line of droplets 1 may be elongate, with gap 3 extending along a length of the elongate shape. In some embodiments, any elongate shape may be chosen, for example a rectangular shape as shown in FIG. 9, an ellipsoidal shape, or a more complex shape. In some embodiments, shapes which are not elongate may also be used, for example a square shape as shown in FIG. 8.

In some embodiments, the exact shape of droplets 1 is selected by control of the pattern of the actuation signals, but may vary from that due to the surface tension between droplets 1 and fluid medium 60, which will depend on the material properties.

In some embodiments, where the shape of the energised contact line of droplets 1 is elongate, the shape of the energised droplets 1 may have an aspect ratio of at least 2:1, preferably at least 4:1 or at least 8:1. In some embodiments, increasing the aspect ratio increases the degree of movement of the surface of droplets 1 when they are de-energised, thereby assisting in bringing droplets 1 into contact.

In some embodiments, gap 3 between droplets 1 in the first stage is chosen such that the two droplets 1 are sufficiently close, although not contacting, that they form droplet interface 2 when placed in the lower energy state. In some embodiments, the width of gap 3 when droplets 1 are brought into proximity is chosen to allow droplets 1 to come into contact when the pattern of actuation signals is changed. In some embodiments, this may depend on the same of the droplets 1 in the energised state. In some embodiments, the width of gap 3 when two droplets 1 are brought into proximity may be chosen so that the centroids of the two droplets 1 are separated by a distance less than the combined radii of the droplets 1 along a line between the two centroids in the lower energy state of the droplets 1.

In some embodiments, gap 3 may have a width of a single row or column of electrodes 48 (e.g., actuation electrodes) in array 50, or two or more rows or columns of electrodes 48 (e.g., actuation electrodes) in array 50.

In some embodiments, to assist these processes, the area enclosed by the contact line of droplets 1 is desirably large compared to the area of electrodes 48 (e.g., actuation electrodes). In some embodiments, this increases the resolution of the control of the shape in the energised state of droplets 1, assisting in allowing movement of droplets 1 across the array and movement of the surfaces of droplets 1 into contact on relaxation. In some embodiments, AM-EWOD device 34 is therefore designed with electrodes 48 (e.g., actuation electrodes) that are sized having regard to typical sizes of droplets 1 desired to be used experimentally. In some embodiments, a particular advantage of the active matrix arrangement is that it allows application of actuation patters of actuation signals at a resolution that is high compared to the size of droplets 1.

In some embodiments, the area enclosed by the contact line of droplets 1 in the lower energy state is at least two times the area of electrode 48 (e.g., actuation electrode), preferably at least 5 times, at least 10 times or at least 20 times. Thus, the area enclosed by the contact line of droplets 1 in the lower energy state may cover at least two electrodes 48 (e.g., actuation electrodes), preferably at least 5 electrodes 48 (e.g., actuation electrodes), at least 10 electrodes 48 (e.g., actuation electrodes), or at least 20 electrodes 48 (e.g., actuation electrodes).

The above description refers, in accordance with certain embodiments, to energising both droplets 1 for ease of description, but alternatively a droplet interface 2 may be formed by only energising one of the two droplets 1 in the first phase. In that case, on changing the actuation signals in the second phase, a surface of that one droplet 1 relaxes into contact with a stationary surface of the other droplet 1, in some embodiments.

Systems of Droplets

Above, there is described, in accordance with certain embodiments, formation of a single droplet interface 2 between a system of two droplets 1. Using similar methods, plural droplet interfaces 2 may be formed between respective pairs of droplets in a system of three or more droplets 1, in some embodiments. In some embodiments, droplet interfaces 2 may be formed sequentially by bringing droplets 1 into contact successively or simultaneously. By way of example, FIG. 13 illustrates an example of forming a system of three droplets 1 having two droplet interfaces 2 that are formed sequentially, and FIG. 14 illustrates an example of forming a system of three droplets 1 having two droplet interfaces 2 that are formed simultaneously. In each of these examples, the droplet interfaces 2 are formed using the method described above.

In some embodiments, the configuration of the formed system of droplets 1 is chosen in a manner to perform a desired experiment. In such formed systems, in some embodiments, droplets 1 may be arranged in series with droplet interfaces 2 similarly in a series, as shown for example in the systems of three droplets 1 shown in FIGS. 13 and 14. Alternatively, in some embodiments, in the formed systems, droplets 1 may have more complex arrangements or clusters, two non-limitative examples of which are shown in FIGS. 15 and 16.

In such systems of droplets 1, the droplets 1 may be or of equal or unequal volume and the droplets 1 may have the same or different constituents.

In some embodiments, one or more droplets in a system may comprise transmembrane pore capable of insertion into a droplet interface 2. In some embodiments, after formation of droplet interface 2, the transmembrane pore inserts spontaneously into droplet interface 2, after which electrical measurements may be taken. In some embodiments, one or more droplets 1 in a system may comprise an analyte that interacts with the transmembrane pore.

In some embodiments, there are a number of advantages in use of the apparatus to form droplet interface 2 and subsequently take electrical measurements on the droplet interface 2 thus formed, in particular when making a system of three or more droplets 1 having plural droplet interfaces 2. For example, in some embodiments, relatively small sample volumes may be used as compared to some other techniques that involve formation of an array of planar membranes. In some embodiments, it allows the possibility of using long lengths of polynucleotide as there is a reduced chance of shearing as library preparation may occur on the same device as measurement. Given that a sample does not need to be transferred, the contamination risks are lower, in some embodiments. Because all of the sample is contained in either one or both of the droplets 1, there is small sample loss, which can be recovered, in some embodiments. In some embodiments, as electro-wetting is used for all liquid manipulation, the need for pumps or other moving parts is eliminated. In some embodiments, since droplet positioning is controlled through programmed scripts, sample preparation can be automated. In some embodiments, droplets of DNA sample can then be supplemented with desired components including polymer vesicles, reagents, pores and analytes.

In one type of experiment, droplets 1 may be periodically split off from a volume of sample, for example to monitor an ongoing reaction occurring in the sample. In some embodiments, this provides for analysis with time, titration of reactant, change in conditions, etc.

Other advantages of certain embodiments include:
the ability to perform coupled library preparation/PCR with sensing/sequencing; ease of use library to sequence (automated, walk away)
low contamination risks
use of compartmentalised samples for library or sequencing
permitting sampling different positions of sample/reaction, for example the length through a gel/mesh/diffusion barrier, positions on a cell sample and/or a concentration/thermal/density gradient.

Lysis

Lysis is a process in which a cell or virus particle is broken down to release its contents such as viral RNA, proteins, enzymes, lipids and cellular DNA. The content of the lysed cell is referred to as the lysate. Various known methods of lysis may be used such as chemical lysis, mechanical disruption such as liquid homogenization, high frequency sound waves, freeze/thaw cycle, manual grinding and electroporation.

In known analysis methods, lysis may form part of the sample preparation and involve specific equipment to provide this function, which increases the complexity of preparation, increases the skill level required to perform analysis and, more importantly, increases the risk of contamination of a sample to be analysed.

In some embodiments, the apparatus or method described herein, alone or in combination, can incorporate a lysing function to release analytes of interest from cells or particles for measurement. In some embodiments, this has a number of advantages such as being able to add sample directly to the device for analysis without the need to pre-lyse, simplify and standardise the overall sample preparation and analysis process. In some embodiments, it can also mitigate the risk of potential contamination by reducing the number of steps to be carried out by the user.

In some embodiments, lysing may be carried out by the use of an electric field. In some embodiments, a droplet containing one or more cells or particles of interest may be actuated with an electrode pair of the apparatus and subjected to an electric field passed between the two electrodes in order to lyse cells.

The droplet is broadly described as being 'actuated' with an electrode pair because a droplet can either contact electrodes directly, or as configured in the examples herein the electrodes are insulated and therefore not in direct contact with the ITO electrodes. In some embodiments, insulated electrodes are preferred. In some embodiments, insulated electrodes can inhibit damage to the ITO. In some embodiments, insulated electrodes can be more durable and retain their performance levels.

The actuation electrodes of the electrowetting apparatus may be used to carry out this lysing function or alternatively the device may further comprise one or more pairs of electrodes that are specific for the task of lysing. Lysing may be carried out using the measurement electrodes. In some embodiments, the means shown herein can additionally lyse cells using spatially and temporally modulated electric fields.

In an example described below, dielectrophoretic live-cell manipulation and electrical cell lysis are integrated with a TFT EWOD array. Thus, a single cell may be introduced as part of a sample within a droplet and carried to an electrode pair, or two or more electrodes. With the droplet positioned above the electrodes, dielectrophoresis (DEP) may be used to align or collate cells within the droplet. The control system may then apply a lysing signal to the droplet to rupture the cells and release the contents, including nucleic acids such as DNA. After lysing, DEP may be used to manage the content of the droplet and selectively manage the DNA therein.

Lysing occurs, in this example, prior to sample preparation for sequencing. The incorporation of lysing functionality, in some embodiments, enables all processes to be automated and take place on one device from start to finish.

Lysis may be carried out using lysing signals having capacitively coupled AC pulses or DC pulses. In some embodiments, lysing signal pulses are generated to inhibit the formation of bubbles in a sample that can occur due to water electrolysis. Moreover, in some embodiments, pulses are generated such that electrochemical erosion or deposition can be inhibited, such that degradation or performance loss is minimised.

In some embodiments, DC pulses enable lysing to occur when an insulating coating is provided over the electrodes because the voltage applied to the electrodes creates an electric field. In some embodiments, the electric field between the electrodes is determined by the voltage applied. In some embodiments, the cells within a droplet that are to be lysed are substantially smaller than the droplet such that the field effect is so great upon the cell that it ruptures. In some embodiments, cells can be aligned using DEP to position cells in areas of maximum field strength. In some embodiments, the coating enables indium-tin oxide (ITO) to be used as an electrode without concern that it will degrade. In some embodiments, the use of non-opaque electrode materials such as ITO permits optical observation of the lysis. A further example of a non-opaque electrode material that may be suitable is graphene.

The apparatus may be optionally configured to apply dielectrophoresis to the droplet in order to separate or collate the one or more cells or particles within the droplet such that they can be efficiently lysed. In some embodiments, the effect of dielectrophoresis causes the cells or particles to move towards and against an electrode and will tend to concentrate the cells or particles to the electrode edge where the field is strongest. The technique is disclosed for example in Pohl and Crane, Biophysical Journal Volume 11 1971, pp 711-727. In some embodiments, the dielectrophoresis field may be advantageously applied between the lysing electrodes to concentrate the cells or particles at the electrodes for lysing. Following grouping of the cells at the electrode surface, in some embodiments, the electrodes may be switched from applying a dielectrophoresis field to applying a DC voltage for lysing. In some embodiments, the cells are lysed rapidly thereafter to reduce any diffusion of analyte from the electrodes following switching off of the dielectrophoresis field. Following lysis to release analyte of interest into the droplet, in some embodiments, a dielectrophoresis field may be re-applied to the droplet to hold released analyte at an electrode. In some embodiments, the lysing electrodes can be used to re-apply the dielectrophoresis field. In some embodiments, any cells that have not been lysed may be separated from the analyte held at the dielectrophoresis electrodes by, for example, activating actuation electrodes that are in contact with the droplet and distal from the dielectrophoresis electrodes.

In some embodiments, the current flowing due to the DEP signal can be measured to give impedance, which is a function of the solution and the particles contained within it. In some embodiments, this can be used to determine the presence of cells, or successful lysis, without the need for optical observation.

Electroporation

In some embodiments, the apparatus can be further configured to transiently electroporate live cells, a technique in which an electrical field is applied to cells in order to increase the permeability of the cell membrane, allowing for example chemicals, drugs, or polynucleotides to be introduced into the cell and can be used to transfect cells. Methods to transfect cells by electroporation are disclosed for example in Curr Protoc Mol Biol. 2003 May; Chapter: Unit-9.3. doi:10.1002/0471142727.mb0903s62. In some embodiments, a droplet containing the cell or cells of interest to be electroporated along with the substance to be introduced into the cell can be subjected to an electric field. In some embodiments, to electroporate the cells, a high DC voltage, which may be in the region of 100V may be momentarily passed between an electrode pair. In some embodiments, electroporation can also be achieved with lower DC voltage levels or even AC voltages. In some embodiments, the electrode pair may be the measurement electrodes. In some embodiments, prior to electroporation, the cell or cells may be initially located at the actuation electrodes by dielectrophoresis.

In some embodiments, samples containing cells or virus particles that are suitable for use with the apparatus of the invention include bodily fluids such as whole blood, plasma, saliva, tears, interstitial fluid, phlegm and urine. In some embodiments, the sample may be liquid or semi-solid. In some embodiments, the cell containing sample may be bacterial, archaeal or eukaryotic in origin and derive from, for example, a mammal, insect, bacteria, virus, yeast, hybridoma or plant.

Long lengths of DNA, for example 500 kbases or greater are susceptible to breakage and need to be handled very carefully. In some embodiments, lysing and measurement in situ within the droplet can eliminate the number of pipetting and transfer steps thus reducing the possibility of fragmenting any DNA released from the cells. This would enable very long strands of DNA to be measured, in some embodiments.

In some embodiments, the apparatus enables samples in droplets to be lysed to result in DNA encapsulation and manipulation in independent aqueous droplets that are movable by EWOD, which enables samples to be isolated and analysed. In some embodiments, the apparatus can support the extraction/characterization of cellular proteins, possibly by sequencing.

Overall, in some embodiments, lysing within the apparatus avoids molecular denaturation due to heat and or chemicals, and reduces mechanical perturbations in general.

Figure 26:
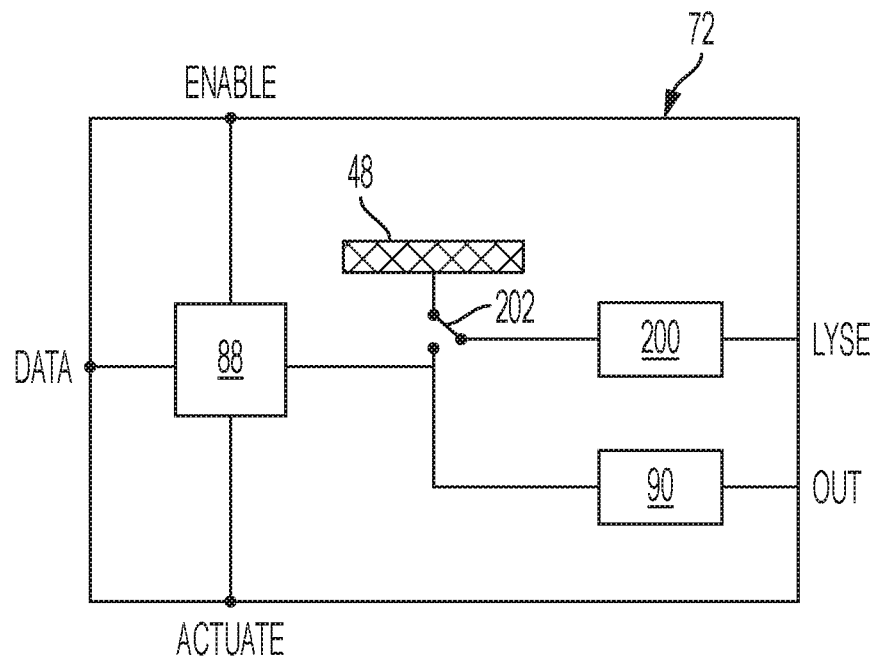
FIG. 26 is, in accordance with certain embodiments, an alternative configuration of FIG. 6 further including a lysing circuit.

FIG. 26 illustrates, in accordance with certain embodiments, the arrangement of array element circuit 72 present in each array element 51. In some embodiments, array element circuit 72 contains actuation circuit 88, having inputs ENABLE, DATA and ACTUATE, and an output from droplet sensing circuit 90 which is connected to electrode 48 (e.g., actuation electrode). In some embodiments, the array circuit element has lysing circuit 200 connected to an actuation electrode via lysing switch 202. In some embodiments, the switch functions to isolate the actuation circuit and sensor circuit from the lysing signal. In some embodiments, the switch can be provided in each circuit, or can be provided in a subset of circuits to provide a lysing signal to a tri-function electrode; the functions including actuation, measurement and lysing. Alternatively, in some embodiments, array element circuit 72 can be provided with a lysing circuit that excludes actuation circuit 88 and droplet sensing circuit 90, such that the circuit is dedicated to two or more electrodes which function to lyse cells in a sample or droplet. An alternative circuit can, additionally, manipulate droplet contents using DEP, in some embodiments.

In some embodiments, electrode 48 and switch 202 are configurable to perform cell lysis. In some embodiments, isolation of the lysing signal allows a high voltage lysing pulse to be applied without disturbing the rest of the system or damaging adjacent hardware. In some embodiments, the high voltage needed to induce cell lysis is generated by a high voltage amplifier module. By way of example. the lysing circuit can be the type used for driving piezo actuators, such as a PDu100B, which is commercially available and sold by Piezo Drive https://www.piezodrive.com/product/pdu100b-miniature-piezo-driver/. In some embodiments, using a 5V power supply, such a module can a 0.7V to 4.3V control voltage to a 0V to 100V lysing signal. In some embodiments, the amplifier of the lysing circuit can have both direct current and capacitively coupled outputs.

In some embodiments, to inhibit offset voltage in the amplifier, a capacitively coupled output is preferred to avoid causing DC current to flow when zero volts is applied. Moreover, in some embodiments, offset voltages have been known to generate DC current between electrodes and/or the top plate, which can degrade the top plate ITO.

In some embodiments, the timing of the lysing pulse is synchronised with the deactivation of the actuation and sensing circuitry such that the signals controlling the droplets is off for the minimum amount of time. In some embodiments, this means the droplet does not have time to relax, so there is negligible droplet or fluid movement during lysing. In addition, in some embodiments, the short high voltage pulse limits electrochemical damage to the ITO electrodes and limits the generation of bubbles by electrolysis.

In some embodiments, the apparatus is operable for single-cell applications, wherein the DNA must first be liberated from a cell prior to adapter ligation and other processing. Known cell lysis involves concentration detergents and denaturing agents that are likely incompatible with the droplet interface bilayer (DIB) membrane stability requirements.

In some embodiments, after receiving a sample in a droplet, the apparatus enables the positioning of droplets and cells over electrodes that are able to apply a lysing signal, wherein a short, high-voltage pulse is applied. In some embodiments, this pulse can function to rupture all membranes around and within the cell.

Figure 27:
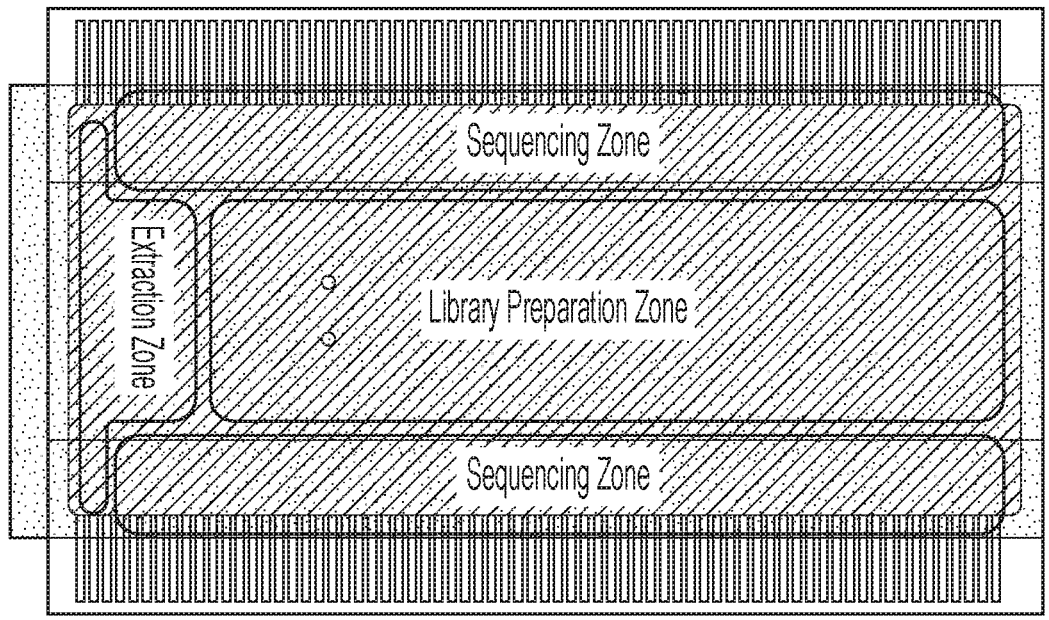
FIG. 27 is, in accordance with certain embodiments, a schematic showing different zones of the device.

FIG. 27 shows, in accordance with certain embodiments, a schematic view of an EWOD device having an extraction zone, two sequencing zones and a library preparation zone. These zones are organisational and can be configured in different regions of the apparatus, in some embodiments. In some embodiments, the functions provided by these zones can overlap. In some embodiments, the functions can be carried out in all areas of the apparatus, such they are not restricted to these zones.

Figure 28:
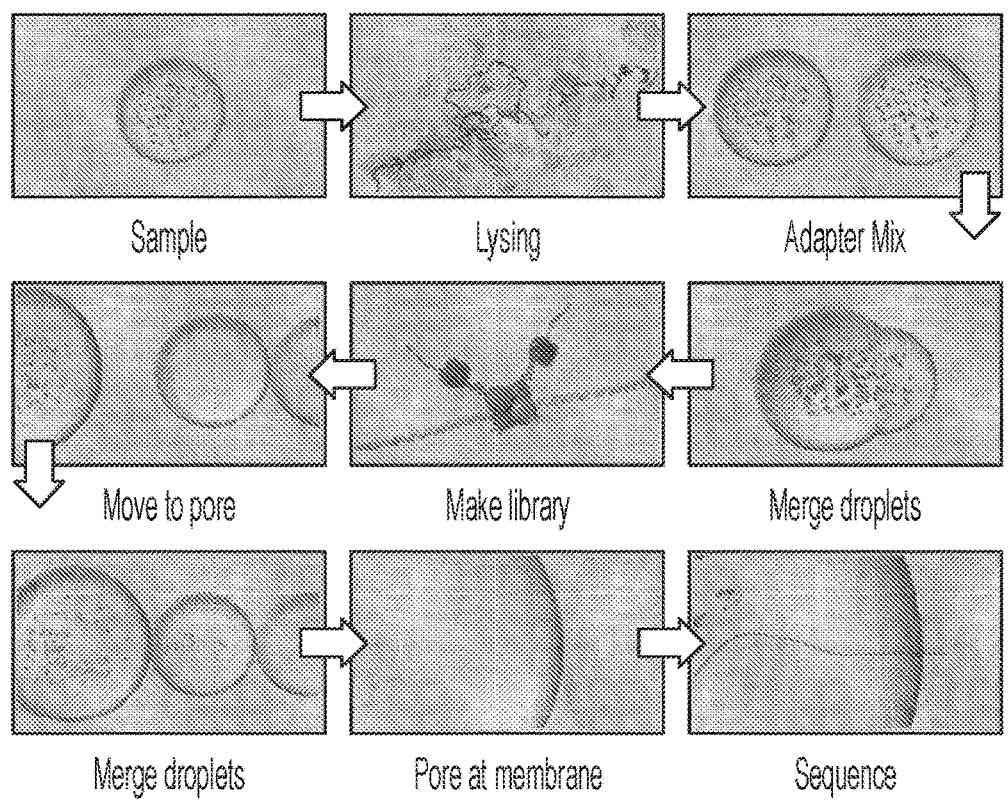
FIG. 28 shows, in accordance with certain embodiments, the steps that the device can take to process a sample.

FIG. 28 is, in accordance with certain embodiments, a schematic illustrating the actions that can be performed on the apparatus. In some embodiments, a sample having cells can be moved to an extraction zone, where cells in a sample can be lysed. In some embodiments, an adapter in a separate droplet can be mixed with the lysed sample to make a library that can be moved to engage with a pore such that a pore is arranged between two droplets in order that the lysed DNA can be sequenced using the pore.

Feedback and Modification

As described above, in some embodiments, the apparatus is suitable for forming droplet interfaces 2 in systems of droplets 1 and performing experiments on those droplet interfaces 2. In some embodiments, particular advantage is obtained by control system 37 modifying a formed system of droplets 1 in response to outputs of droplet interface sensor system 110. Thus, in some embodiments, the system of droplets 1 may be modified to modify ongoing performance of the experiments using feedback from the experiment previously performed. This provides a powerful experimental tool, because the experiments may be adaptively performed.

In some embodiments, various outputs of droplet interface sensor system 110 may be used to provide feedback, for example as follows.

In some embodiments, the outputs of droplet interface sensor system 110 that may be used include electrical measurements taken by measurement unit 111. In some embodiments, this provides a first type of control. As the electrical properties are fundamental to the relevant processes such as formation of droplet interfaces and reactions occurring there, this first type of control allows those processes to be considered and adaptively modified, in some embodiments. For example, in some embodiments, electrical measurements taken by the sensor system may be used to determine whether droplet interface 2 has been formed successfully.

In some embodiments, the outputs of droplet interface sensor system 110 that may be used include outputs of analysis system 112. In some embodiments, this provides a second type of control. As such analysis allows higher level information to be obtained, for example concerning an analyte being analysed, this second type of control provides powerful experimental adaption based on the results of the analysis, in some embodiments.

In some embodiments, control system 37 may modify a formed system of droplets 1 in various ways, for example as follows.

In some embodiments, control system 37 may modify a formed system of droplets 1 by separating droplet interface 2 between in the system. To do this, in some embodiments, control system 37 applies a pattern of actuation signals to electrodes 48 (e.g., actuation electrodes) that moves apart one or both droplets between which droplet interface 2 is formed. In some embodiments, the separation of droplets 1 separates droplet interface 2.

Such separation may be used, for example, to stop an interaction occurring at droplet interface 2. This may be done, for example, when the electrical measurements taken by measurement unit 111 indicate that droplet interface 2 has not been formed successfully or the outputs of analysis system 112 indicate that an analysis has been completed, for example because an analyte has become depleted, or sufficient electrical measurements about a particular analyte have been taken.

In some embodiments, control system 37 may modify a formed system of droplets 1 by moving a new droplet 1 into contact with a current droplet 1 in the system of droplets 1 and forming droplet interface 2 between the new droplet 1 and the current droplet 1. To do this, in some embodiments, control system 37 applies actuation signals to electrodes 48 (e.g., actuation electrodes) using the same method as described above.

Such formation of a new droplet interface 2 may be used, for example, when the electrical measurements taken by measurement unit 111 indicate that droplet interface 2 has not been formed successfully so it desired to form a new droplet interface, or the outputs of analysis system 112 indicate that an analysis at droplet interface 2 has been completed and it is desired to obtain further measurements.

In some embodiments, control system 37 may modify a formed system of droplets 1 by moving a new droplet 1 into contact with a current droplet 1 in the system of droplets 1 and fusing new droplet 1 and current droplet 1. To do this, in some embodiments, control system 37 applies actuation signals to electrodes 48 (e.g., actuation electrodes) that moves new droplet 1 into contact with current droplet 1 and causes them to fuse. In some embodiments, the fusing of droplets 1 may be achieved simply by the movement of new droplet 1 into contact with current droplet 1 without using the method described above to form a droplet interface. Alternatively, or additionally, in some embodiments, the fusing of droplets 1 may be achieved by applying an AC actuation signal that ruptures the droplet interface that would otherwise be formed between new droplet 1 and the current droplet.

In some embodiments, such fusing of new droplet 1 into current droplet 1 of the system may be used, for example, to introduce new reagents into current droplet 1, for example when one member of a redox couple in the one of the pairs of droplets 1 has become depleted.

In some embodiments, when fusing new droplet 1 in this manner, it may be that new droplet 1 does not comprise amphipathic molecules at the interface between the liquid of droplet 1 and fluid medium 60.

In some embodiments, these and other ways of modifying the formed system of droplets 1 may be used together in any combination, for example to perform a multi-stage experiment.

Although some specific applications are described above, these are not limitative and indeed one of the benefits of the feedback is that versatility. Some further non-limitative examples of applications are as follows:

Automated insertion of transmembrane pores
Adaption of a system of droplets 1 to unwanted insertion of pores or secondary pores
Control based on reaction/sample conditions
Promotion of droplet interface separation
Delivery of more sample or reagent
Delivery of a different sample
Delivery of more mediator to a droplet
Separation of a droplet 1 to take a sample elsewhere and/or to recover it and/or to return it to an original volume of sample
Change of reaction conditions (e.g. temperature, additive, quench/activate)
Taking of an alternative measurement (e.g. absorbance)
Return of sample to original volume
Performance of a new reaction on an analysed sample (or part thereof)
Control of multiple pore types and balancing of each for multiple membranes
Formation of membrane arrangements with multiple membranes and pores that interfaces with the same sample
Performance of an experiment only until sufficient information has been obtained, thereby increasing overall experimental throughput.
Queuing/pooling of samples, e.g. allowing delivery of library samples from a queue of samples on demand, and/or changing the queue order
Pooling of samples as a result of sequencing/sensing
Determination of which of plural samples to analyse
Determination of duration of run/success criteria
Determination of conditions for sample modification prior to membrane/pore analysis (e.g. type/concentration of library prep)
When droplets 1 are periodically split off from a volume of sample, use of the result of previous experiments as feedback to adapt reaction/sample conditions
Performance of directed evolution using membrane/pore as sensor Droplets in Fluid Medium Where reference is herein to droplets comprising liquid in a fluid medium, the liquid and the fluid medium may be chosen as follows. In some embodiments, any liquid that forms a droplet in a fluid medium may be used, but some possible materials are as follows.

The fluid medium may in principle be a gaseous medium, but is preferably a liquid medium.

In some cases, and often when the fluid medium is a liquid medium, one of the liquid and the fluid medium is polar, and the other of the liquid and the fluid medium is apolar. Preferably, the liquid of the droplets is polar, and the fluid medium is apolar.

When one of the liquid and the fluid medium is polar, the polar medium is, in some embodiments, an aqueous liquid that comprises water. In some embodiments, the aqueous liquid may further comprise one or more solutes. The aqueous liquid may for instance comprise a buffer in order to regulate the pH of the aqueous medium as appropriate, and it may comprise a supporting electrolyte. The aqueous medium may for instance comprise a redox couple, or a member of a redox couple which may be partially oxidised or reduced to provide the redox couple. In some embodiments, the redox couple may be chosen from those known in the art such as $Fe^{2+}/Fe^{3+}$, ferrocene/ferrocenium or $Ru^{2+}/Ru^{3+}$. Examples of such are ferro/ferricyanide, ruthenium hexamine and ferrocene carboxylic acid.

Alternatively, when one of the liquid and the fluid medium is polar, the polar medium may comprise a polar organic solvent, in some embodiments. In some embodiments, the polar organic solvent may for instance be a protic organic solvent, such as an alcohol, or it may be an aprotic polar organic solvent.

In some embodiments, the liquid of the droplets may be any liquid suitable for performing experiments of the type described below. In some embodiments, different droplets may comprise different liquids.

In some embodiments, where the other of the liquid and the fluid medium is apolar, then the apolar medium may comprise an oil. In some embodiments, the oil may be a single compound, or the oil may comprise a mixture of two or more compounds.

In one example, the oil is pure alkane hydrocarbon.

The oil may for instance comprise silicone oil. Suitable silicone oils include, for instance, poly(phenyl methyl siloxane) and poly(dimethylsiloxane) (PDMS). In some embodiments, the silicone oil may comprise a hydroxy-terminated silicone oil, for instance hydroxy terminated PDMS.

Additionally or alternatively, in some embodiments, the oil may comprise a hydrocarbon, for instance hexadecane, although any suitable hydrocarbon may be used. When the oil comprises a hydrocarbon it may comprise a single hydrocarbon compound, or a mixture of two or more hydrocarbons. When the oil comprises a hydrocarbon, the hydrocarbon may be branched or unbranched. The hydrocarbon may, for instance, be squalene, hexadecane or decane. In one embodiment it is hexadecane. However, in some embodiments the hydrocarbon may be substituted with a halogen atom, for instance bromine.

In some embodiments, the oil may comprise a mixture of one or more silicone oils and one or more hydrocarbons. In some embodiments, the silicone oil and hydrocarbon in the mixture may both be as further defined above. The silicone oil may for instance be poly(phenyl methyl siloxane) or PDMS.

In some embodiments, other types of oil are also possible. For example, the oil may be a fluorocarbon or a bromo-substituted $C_{10}$-$C_{30}$ alkane, in some embodiments.

Amphipathic Molecules

In the case that one of the liquid and the fluid medium is polar, and the other of the liquid and the fluid medium being apolar, then the droplets may further comprise amphipathic molecules at the interface between the liquid of the droplets and the fluid medium, in some embodiments. In some embodiments, such amphipathic molecules serve to stabilise the droplets in the fluid medium prior to formation of a droplet interface. Also, in some embodiments, the amphipathic molecules may allow the droplet interface, when formed, to comprise a membrane of amphipathic molecules.

Numerous different types of amphipathic molecules may be used. Some non-limiting examples of types of amphipathic molecules that may be used are as follows.

In one example, the amphipathic molecules may comprise a lipid, which may have a single component or a mixture of components, as is conventional when forming lipid bilayers.

In some embodiments, any lipids that form a membrane such as a lipid bilayer may be used. In some embodiments, the lipids are chosen such that a lipid bilayer having the required properties, such as surface charge, ability to support membrane proteins, packing density or mechanical properties, is formed. In some embodiments, the lipids can comprise one or more different lipids. For instance, in some embodiments, the lipids can contain up to 100 lipids. In some embodiments, the lipids preferably contain 1 to 10 lipids. In some embodiments, the lipids may comprise naturally-occurring lipids and/or artificial lipids.

In some embodiments, the lipids can also be chemically-modified.

In some embodiments, amphipathic polymer membranes are preferred over lipid membranes due to their ability to withstand higher voltages.

In another example, the amphipathic molecules may comprise an amphipathic compound comprising a first outer hydrophilic group, a hydrophobic core group, and a second outer hydrophilic group, wherein each of the first and second outer hydrophilic groups is linked to the hydrophobic core group.

Some such amphipathic compounds are disclosed in WO 2014/064444.

Other such amphipathic compounds are disclosed in U.S. Pat. No. 6,916,488 which is incorporated herein by reference and discloses a number of polymeric materials that can be employed in the apparatus, in some embodiments, as planar amphipathic membranes. In particular, triblock copolymers are disclosed, for example silicon triblock copolymer membranes such as poly(2-methyloxazoline)-block-poly(dimethylsiloxane)-block-poly(2-methyloxazoline) (PMOXA-PDMS-PMOXA).

Examples of silicone triblock polymers that may be employed are 7-22-7 PMOXA-PDMS-PMOXA, 6-45-6 PMOXA-PE-PMOXA and 6-30-6 PMOXA-PDMS-PMOXA, where the nomenclature refers to the number of subunits.

In some embodiments, such triblock copolymers may be provided in vesicle form in the droplets.

Depending on the nature of the amphipathic molecules, the membranes may be bilayers of the amphipathic molecules or may be monolayers of the amphipathic molecules, in some embodiments.

In some embodiments, the amphipathic molecules may alternatively be replaced by another surfactant.

In some embodiments, different droplet interfaces may comprise membranes of different amphipathic molecules, for example membranes comprising a lipid bilayer and a polymer membrane such as a silicone triblock polymer membrane as described above, such as disclosed in WO2017/004504.

In some embodiments, the electrical measurements that are taken may be used to study the membrane of amphipathic molecules itself, or interactions thereof, for example to study drug-membrane permittivity.

Transmembrane Pore

In some embodiments, any transmembrane pore may be used that is capable of inserting into the droplet interface. Different droplets may comprise the same or different transmembrane pore, so that when plural droplet interfaces are formed between different plural droplet pairs, the same or different transmembrane pore may insert into those droplet interfaces.

Some non-limitative examples of types of transmembrane pore that may be used are as follows.

A transmembrane pore is a channel structure that provides a pathway from one of a membrane to the other through which ions may flow. In some embodiments, the channel may vary in width along its length and has an inner diameter of between 0.5 nm and 10 nm.

In some embodiments, any suitable transmembrane pore may be used in the invention. In some embodiments, the pore may be biological or artificial. Suitable pores include, but are not limited to, protein pores, polynucleotide pores and solid state pores. In some embodiments, the pore may be a DNA origami pore (Langecker et al., Science, 2012; 338: 932-936). Suitable DNA origami pores are disclosed in WO2013/083983.

In some embodiments, the transmembrane pore is preferably a transmembrane protein pore.

In some embodiments, the transmembrane protein pore may be a monomer or an oligomer. In some embodiments, the pore may be a hexameric, heptameric, octameric or nonameric pore. In some embodiments, the pore may be a homo-oligomer or a hetero-oligomer.

In some embodiments, the transmembrane protein pore may be derived from CsgG, such as from CsgG from *E. coli* Str. K-12 substr. MC4100. Examples of suitable CsgG pores are described in WO-2016/034591, WO-2017/149316, WO-2017/149317 and WO-2017/149318.

In some embodiments, the transmembrane protein pore comprises a barrel or channel through which the ions may flow. In some embodiments, the subunits of the pore surround a central axis and contribute strands to a transmembrane β barrel or channel or a transmembrane α-helix bundle or channel.

In some embodiments, the barrel or channel of the transmembrane protein pore comprises amino acids that facilitate interaction with an analyte, such as a nucleotide, polynucleotide or nucleic acid. In some embodiments, the pore may be modified by, for example, substitution or deletion of one of more amino acids.

In some embodiments, transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin.

In some embodiments, the transmembrane pore may be derived from or based on Msp, α-hemolysin (α-HL), lysenin, CsgG, ClyA, Sp1 and haemolytic protein fragaceatoxin C (FraC). In some embodiments, the transmembrane protein pore is preferably derived from CsgG, more preferably from CsgG from *E. coli* Str. K-12 substr. MC4100.

In some embodiments, the transmembrane pore may be derived from lysenin. Suitable pores derived from lysenin are disclosed in WO 2013/153359.

In some embodiments, the pore may be a variant of the above listed nanopores. In some embodiments, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence.

In some embodiments, standard methods in the art may be used to determine homology. For example, the UWGCG Package provides the BESTFIT program which can be used to calculate homology, for example used on its default settings (Devereux et al (1984) *Nucleic Acids Research* 12, p 387-395). In some embodiments, the PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/). In some embodiments, similarity can be measured using pairwise identity or by applying a scoring matrix such as BLOSUM62 and converting to an equivalent identity. Since they represent functional rather than evolved changes, deliberately mutated positions would be masked when determining homology, in some embodiments. In some embodiments, similarity may be determined more sensitively by the application of position-specific scoring matrices using, for example, PSIBLAST on a comprehensive database of protein sequences. In some embodiments, a different scoring matrix could be used that reflect amino acid chemicophysical properties rather than frequency of substitution over evolutionary time scales (e.g. charge).

In some embodiments, amino acid substitutions may be made to the amino acid sequence of SEQ ID NO: 3, for example up to 1, 2, 3, 4, 5, 10, 20 or 30 substitutions. In some embodiments, conservative substitutions replace amino acids with other amino acids of similar chemical structure, similar chemical properties or similar side-chain volume. In some embodiments, the amino acids introduced may have similar polarity, hydrophilicity, hydrophobicity, basicity, acidity, neutrality or charge to the amino acids they replace. Alternatively, in some embodiments, the conservative substitution may introduce another amino acid that is aromatic or aliphatic in the place of a pre-existing aromatic or aliphatic amino acid.

In some embodiments, any of the proteins described herein, such as the transmembrane protein pores, may be made synthetically or by recombinant means. For example, in some embodiments, the pore may be synthesised by in vitro translation and transcription (IVTT). In some embodiments, the amino acid sequence of the pore may be modified to include non-naturally occurring amino acids or to increase the stability of the protein. In some embodiments, when a protein is produced by synthetic means, such amino acids may be introduced during production. In some embodiments, the pore may also be altered following either synthetic or recombinant production.

In some embodiments, any of the proteins described herein, such as the transmembrane protein pores, can be produced using standard methods known in the art. In some embodiments, polynucleotide sequences encoding a pore or construct may be derived and replicated using standard methods in the art. In some embodiments, polynucleotide sequences encoding a pore or construct may be expressed in a bacterial host cell using standard techniques in the art. In some embodiments, the pore may be produced in a cell by in situ expression of the polypeptide from a recombinant expression vector. In some embodiments, the expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

In some embodiments, the pore may be produced in large scale following purification by any protein liquid chromatography system from protein producing organisms or after recombinant expression. In some embodiments, typical protein liquid chromatography systems include FPLC, AKTA systems, the Bio-Cad system, the Bio-Rad BioLogic system and the Gilson HPLC system.

Analyte

In some embodiments, the droplets may comprise an analyte that is capable of interaction with the transmembrane pore, also referred to as a target analyte, the template analyte or the analyte of interest. For example, in some embodiments, the analyte may be a polymer or a drug.

In some embodiments, electrical measurements that are taken may be dependent on the interaction of the analyte with the transmembrane pore. In some embodiments, the electrical measurements may be measurements of ion current through the pore.

In some embodiments, there the electrical measurements are dependent on the interaction of the analyte with the transmembrane pore, the analysis may determine the presence, absence or one or more characteristics of a target analyte. In some embodiments, the analysis may determine the presence, absence or one or more characteristics of a target analyte. In some embodiments, where the analyte is a polymer comprising polymer units, in the analysis the electrical measurements may be processed to derive estimated identities of the polymer units, or to count polymer units or determine length of the polymer. In some embodiments, control experiments can be carried out in the presence of different analytes or polymer units, to determine how analytes affect the electrical measurements as the basis for the analysis.

In some embodiments, the analysis may be performed using any suitable known technique, including techniques employing a Hidden Markov Model, for example as described in WO-2013/041878 or WO-2015/140535; techniques employing machine learning for example as described in Boza et al., "DeepNano: Deep recurrent neural networks for base calling in MinION nanopore reads", PLoS ONE 12(6): e0178751, 5 Jun. 2017; techniques employing comparison of feature vectors for example as described in WO-2013/121224; or any other suitable technique.

In some embodiments, such interaction may occur as an analyte moves with respect to, such as translocating through, the pore. In that case, in some embodiments, the electrical measurements may be taken as the analyte moves with respect to the pore. In some embodiments, such movement may occur while a potential difference is applied between the droplets, i.e. across the pore. The applied potential results, in some embodiments, in the formation of a complex between the pore and a polynucleotide binding protein. In some embodiments, the applied potential difference may be a voltage potential. Alternatively, in some embodiments, the applied potential difference may be a chemical potential. An example of this is using a salt gradient across an amphiphilic layer. A salt gradient is disclosed in Holden et al., J Am Chem Soc. 2007 Jul. 11; 129(27):8650-5.

In some embodiments, the target analyte may be a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

In some embodiments, the analyte may be an amino acid, a peptide, a polypeptides and/or a protein. The amino acid, peptide, polypeptide or protein can be naturally-occurring or non-naturally-occurring. In some embodiments, the polypeptide or protein can include within them synthetic or modified amino acids. A number of different types of modification to amino acids are known in the art. Suitable amino acids and modifications thereof are described above. For the purposes of the invention, it is to be understood that the target analyte can be modified by any method available in the art, in some embodiments.

In some embodiments, the analyte protein can be an enzyme, an antibody, a hormone, a growth factor or a growth regulatory protein, such as a cytokine. In some embodiments, the cytokine may be selected from interleukins, preferably IFN-1, IL-1, IL-2, IL-4, IL-5, IL-6, IL-10, IL-12 and IL-13, interferons, preferably IL-$\gamma$, and other cytokines such as TNF-$\alpha$. In some embodiments, the protein may be a bacterial protein, a fungal protein, a virus protein or a parasite-derived protein.

In some embodiments, the target analyte may be a nucleotide, an oligonucleotide or a polynucleotide. Nucleotides and polynucleotides are discussed below. Oligonucleotides are short nucleotide polymers which typically have 50 or fewer nucleotides, such 40 or fewer, 30 or fewer, 20 or fewer, 10 or fewer or 5 or fewer nucleotides. In some embodiments, the oligonucleotides may comprise any of the nucleotides discussed below, including the abasic, and modified, nucleotides.

In some embodiments, at least a portion of the polynucleotide may be double stranded.

In some embodiments, the polynucleotide can be a nucleic acid, such as deoxyribonucleic acid (DNA) or ribonucleic acid (RNA). In some embodiments, the polynucleotide can comprise one strand of RNA hybridised to one strand of DNA.

In some embodiments, the polynucleotide can be any length. For example, in some embodiments, the polynucleotide can be at least 10, at least 50, at least 100, at least 500 nucleotides or nucleotide pairs in length. In some embodiments, the polynucleotide can be 1000 or more, 10000 or more, 100000 or more, or 1000000 or more nucleotides or nucleotide pairs in length.

Any number of polynucleotides can be investigated. For instance, in some embodiments, the method of the invention may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial.

In some embodiments, where the analyte is a polynucleotide comprising nucleotides and estimated identities of the polymer units are derived from the electrical measurements, then strand characterisation/sequencing or exonuclease characterisation/sequencing may be applied.

In some embodiments, in strand sequencing, the polynucleotide may be translocated through the nanopore either with or against an applied potential. In this case, in some embodiments, the electrical measurements are indicative of one or more characteristics of multiple nucleotides.

In some embodiments, the droplets may contain a polymer binding moiety such as an enzyme to control translocation of the polymer through the pore. In some embodiments, the moiety can be a molecular motor using for example, in the case where the moiety is an enzyme, enzymatic activity, or as a molecular brake.

In some embodiments, where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used in some embodiments. In some embodiments, the polymer interacting moiety may be any disclosed in WO-2010/086603, WO-2012/107778, and Lieberman K R et al, J Am Chem Soc. 2010; 132(50):17961-72), and for voltage gated schemes (Luan B et al., Phys Rev Lett. 2010; 104(23): 238103).

In some embodiments, the polymer binding moiety can be used in a number of ways to control the polymer motion. In some embodiments, the moiety can move the polymer through the nanopore with or against the applied field. In some embodiments, the moiety can be used as a molecular motor using for example, in the case where the moiety is an enzyme, enzymatic activity, or as a molecular brake. In some embodiments, the translocation of the polymer may be controlled by a molecular ratchet that controls the movement of the polymer through the pore. In some embodiments, the molecular ratchet may be a polymer binding protein. For polynucleotides, the polynucleotide binding protein is preferably a polynucleotide handling enzyme, in some embodiments.

In some embodiments, preferred polynucleotide handling enzymes are polymerases, exonucleases, helicases and topoisomerases, such as gyrases. In some embodiments, a polynucleotide handling enzyme may be for example one of the types of polynucleotide handling enzyme described in WO-2015/140535 or WO-2010/086603.

In an embodiment, one or more of the membranes may be a selective membrane having multiple pores inserted to provide a kind of frit alternative to supply a reagent. This embodiment may be employed for example in a three pore system comprising a droplet pair and a third droplet connected to a droplet of the pair, whereby the interface between the third droplet and the droplet of the pair comprises multiple pores. The third droplet may for example comprise an electrochemical mediator such as ferricyanide $[Fe(CN)_6]^{3-/2-}$.

In some embodiments, different droplet interfaces may have different transmembrane pores inserted thereon.

Coupling

In some embodiments, the analyte may contain an anchor to couple it to a membrane, or a tether to couple it to a pore. In some embodiments, the membrane may be functionalised to facilitate coupling of an analyte. In some embodiments, the pore may be modified to facilitate tethering of the analyte. In some embodiments, methods of coupling an analyte to a membrane that are known in the art may be used, for example as described in WO-2012/164270 or WO-2015/150786. In some embodiments, methods of tethering an analyte to a pore that are known in the art may be used, for example as described in WO-2012/164270 or PCT/GB2017/053603.

Sample

In some embodiments, droplets 1 may be prepared from a sample. In some embodiments, such a sample may be known to contain or suspected to contain an analyte In some embodiments, the sample may be a biological sample. In some embodiments, the sample may be obtained from or extracted from any organism or microorganism.

In some embodiments, the sample may be obtained from or extracted from any virus.

In some embodiments, the sample is preferably a fluid sample. In some embodiments, the sample comprises a body fluid of the patient. In some embodiments, the sample may be urine, lymph, saliva, mucus or amniotic fluid but is preferably blood, plasma or serum.

In some embodiments, the sample may be human in origin, but alternatively it may be from another mammal animal such as from commercially farmed animals such as horses, cattle, sheep, fish, chickens or pigs or may alternatively be pets such as cats or dogs. Alternatively, in some embodiments, the sample may be of plant origin, such as a sample obtained from a commercial crop, such as a cereal, legume, fruit or vegetable.

In some embodiments, the sample may be, or may derived from, a non-biological sample. In some embodiments, the non-biological sample is preferably a fluid sample. Examples of non-biological samples include surgical fluids, water such as drinking water, sea water or river water, and reagents for laboratory tests.

The following examples are intended to illustrate certain embodiments of the present invention, but do not exemplify the full scope of the invention.

Example 1

An Example of use of the apparatus which has been carried out is as follows.

The apparatus of the Example was designed to perform DNA sample preparation and sequencing in one, portable platform. The key sequencing element was a protein nanopore embedded in a polymer membrane that was formed at droplet interface 2 between two aqueous droplets 1 in AM-EWOD device 34 of the type described above.

In this Example, the liquid of droplets 1 was aqueous solution, the droplets contained amphipathic molecules that were triblock copolymers of the type describe above in vesicle form, and fluid medium 60 was pure alkane hydrocarbon.

The Example used AM-EWOD device 34 having array 50 of electrodes 48 (e.g., actuation electrodes) as shown in FIG. 17 which are images also showing two droplets 1. FIG. 17a was taken at the end of the first stage of the method described above with the droplets 1 in the energised state in proximity with gap 3 therebetween. FIG. 17b was taken after the end of the second stage when droplets 1 have relaxed to form droplet interface 2. Each electrode 48 (e.g., actuation electrode) in the array was of dimensions 200×200 μm and thus much smaller than any droplet 1 used.

In AM-EWOD device 34, layer 58 of conductive material was patterned as shown in FIG. 18, wherein box 120 shows the region where the images of FIG. 17 were taken. FIG. 18 shows contact pads 121 labelled C1 through C15 at the top edge. Sensor electrode 100 connected to contact pads 121 labelled C2 (grounded) and sensor electrode 100 connected to contact pads 121 labelled C5 (recording) were used for electrical recording from droplet interface 2 in panel FIG. 17b.

Recording electrodes were integrated into AM-EWOD device 34 to facilitate voltage application and the current recording that comprises the pore DNA sequencing signal.

In the Example, current recording was performed on individual droplet interfaces 2 using a standard patch clamp amplifier. For multichannel recording from an array of droplet interfaces 2 in parallel, a multichannel recording system can be employed, in some embodiments. In some embodiments, to enable recording of sufficient quality for DNA sequencing (<1 pA rms@5 KHz), the system must be virtually free of electrical noise. Therefore, preferentially, the apparatus operates in two mutually exclusive modes, referred to as an EWOD mode and a recording mode, in some embodiments.

In some embodiments, in the EWOD mode, all features in layer 58 of conductive material are connected to control electronics 38 which supplies a part of the voltage necessary for movement. Because EWOD uses high frequency, large AC voltage fields, recording cannot take place while the EWOD field is on, in some embodiments. Specifically, the EWOD field generates noise that obscures the DNA signal, in some embodiments. Therefore, in some embodiments, once the droplets 1 are positioned as desired, the control electronics 38 is unplugged, although internal switching components could alternatively be used. Once EWOD is unplugged, multipole switches are actuated.

The entire apparatus was enclosed in a Faraday cage during recording to prevent interference from ambient noise. Thus, during recording mode, the droplets are not held in place by any electrically induced forces, in some embodiments.

Using the method described above, AM-EWOD device 34 was used to create three systems each consisting of two droplets 1 having droplet interfaces 2 therebetween, as shown in FIG. 19.

Formation of droplet interfaces 2 was performed as follows.

Simply manipulating two droplets 1 to bring them together under the application of actuation signals to electrodes 48 (e.g., actuation electrodes) was possible, but challenging because the droplets 1 tended to fuse.

Instead, the method described above was used. Specifically, in the first stage, droplets 1 were energised into rectangular shapes with an aspect ratio greater than 1.5. The long edges of these shapes were brought into 1-2 pixel proximity and centered. An example of this stage applied to three droplets 1 is shown in FIG. 20, left hand side.

In the second stage, the actuation signals were switched. The droplets naturally relaxed back into relaxed circular shapes to reduce their surface area to volume ratio. Relaxation caused the surfaces of the droplets facing each other across the gaps 3 to contact and form a droplet interface 2 (which may be referred to as passive formation). Using this approach, DIBs may be created between two or more droplets, in some embodiments. An example of this stage applied to three droplets 1 is shown in FIG. 20, right hand side.

Such formation of droplet interfaces 2 was a reversible process.

Although control electronics 38 produced noise that would obscure the DNA sequencing signal, it is still possible to observe a large current event, such as pore insertion into droplet interface 2. As a demonstration, the apparatus was set up such that AM-EWOD device 34 could be powered to a low noise mode and droplets were positioned to form a droplet interface while recording electrical current.

Figure 21:
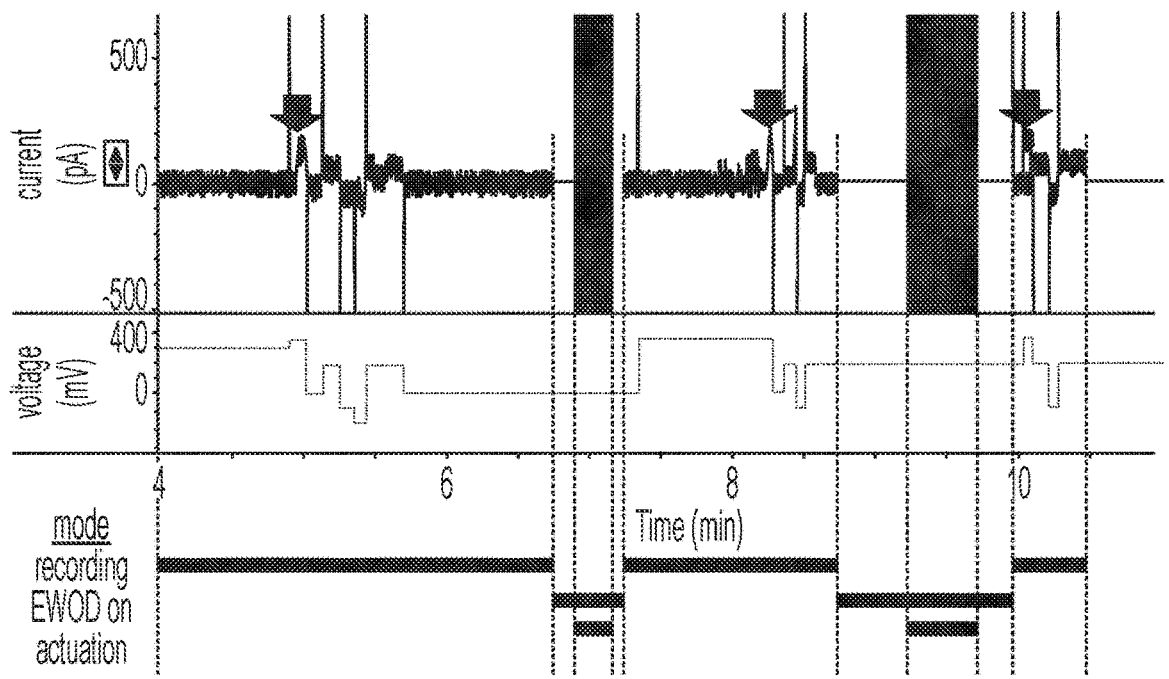
FIG. 21 is, in accordance with certain embodiments, a plot of electrical measurements of current and voltage during formation, separation and re-formation of droplet interfaces in the AM-EWOD device.

FIG. 21 shows the electrical current thus recorded. Within this signal it is possible to observe formation of droplet interfaces 2, unzipping, reformation and pore insertion. Multiple cycles of pore insertion and membrane disconnect and reconnect are shown. Thick black arrows denote pore insertion. The recording time bars indicate recording mode, the EWODon time bars represent EWOD mode and the actuation time bars indicate droplet actuation and shaping. Off-scale noise was observed during droplet actuation.

Pore insertion was observed as a jump in current from 0 to ~200 pA at 300 mV. After pore insertion, voltage was switched to zero and the system switched to EWOD mode. Droplets 1 were separated, and then a droplet interface was reformed. Note that during this time, the noise goes beyond the scale of the current recording instrument.

The system was then switched back to recording mode and a voltage of 300 mV applied. After observing another pore insertion, the cycle was repeated once more for a total of three pore insertions and two separations of droplet interfaces 2. This demonstrates the ability to form droplet interfaces 2, insert pores, separate droplets 1 and reform droplet interfaces 2 repeatedly in the AM-EWOD device 34.

DNA detection and sequencing was performed as follows.

By placing the amphipathic molecules in droplets 1 rather than fluid medium 60, it becomes possible to make asymmetric membranes, in some embodiments. For example, in some embodiments, the DNA droplet could have a lower concentration of polymer vesicle relative to the opposing droplet or it could have an entirely different polymer composition. This may provide flexibility in optimizing sample prep, DIB formation, pore insertion, DNA sequencing or further processes, in some embodiments.

Figure 22:
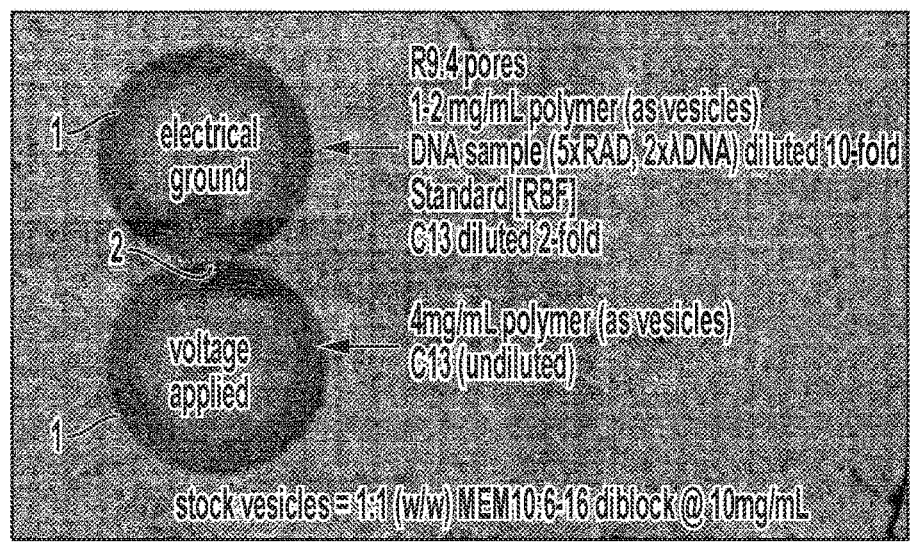
FIG. 22 is, in accordance with certain embodiments, an image of a system of two droplets in the AM-EWOD device.

In one example, an asymmetric pair of droplets 1 was used as shown in FIG. 22 to detect short DNA strands (adapter). FIG. 22 shows an example of droplet interface 2 comprising a membrane of amphipathic molecules having a concentration below 2 mg/mL in the DNA droplet (top) to aids pore insertion. Higher polymer concentration in the opposing droplet (bottom) aids stability.

Figure 23:
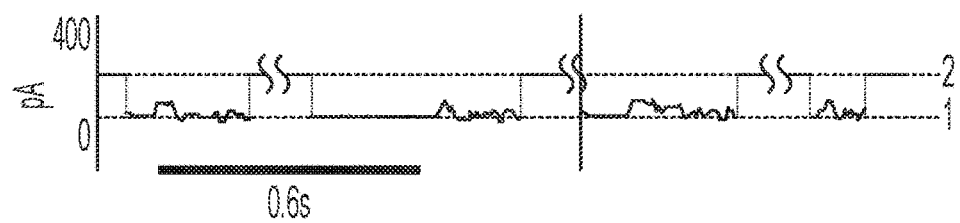
FIG. 23 is, in accordance with certain embodiments, a trace of a current signal obtained in the system of droplets in FIG. 22.

FIG. 23 shows an example of the characteristic adapter signal obtained from the droplet interface in FIG. 22. Current levels, shown in pA, represent the open pore (2) and an adapter-occupied pore. In FIG. 23, the characteristic squiggle of the adapter blockade is an easily recognizable signal that established the quality of the pore and overall system configuration.

In some embodiments, the same approach can be applied to obtain sequencing signals from single strands of DNA. A droplet interface 2 was created from a droplet 1 containing a 3.6 Kb single-strand DNA sample, sequencing reagents and enzymes, polymer vesicles, mediator buffer and nanopores. The opposing droplet 1 contained vesicles of amphipathic molecules and mediator+salts to osmotically balance with the DNA droplet 1.

After observing a single pore insertion, the control electronics 38 were unplugged and electrodes switched to recording mode. During sequencing, a strand of DNA threads into the pore which is then pulled through by the applied voltage. The speed of threading is regulated by an attached enzyme that is, in turn, powered by ATP turnover in the droplet.

Figure 24:
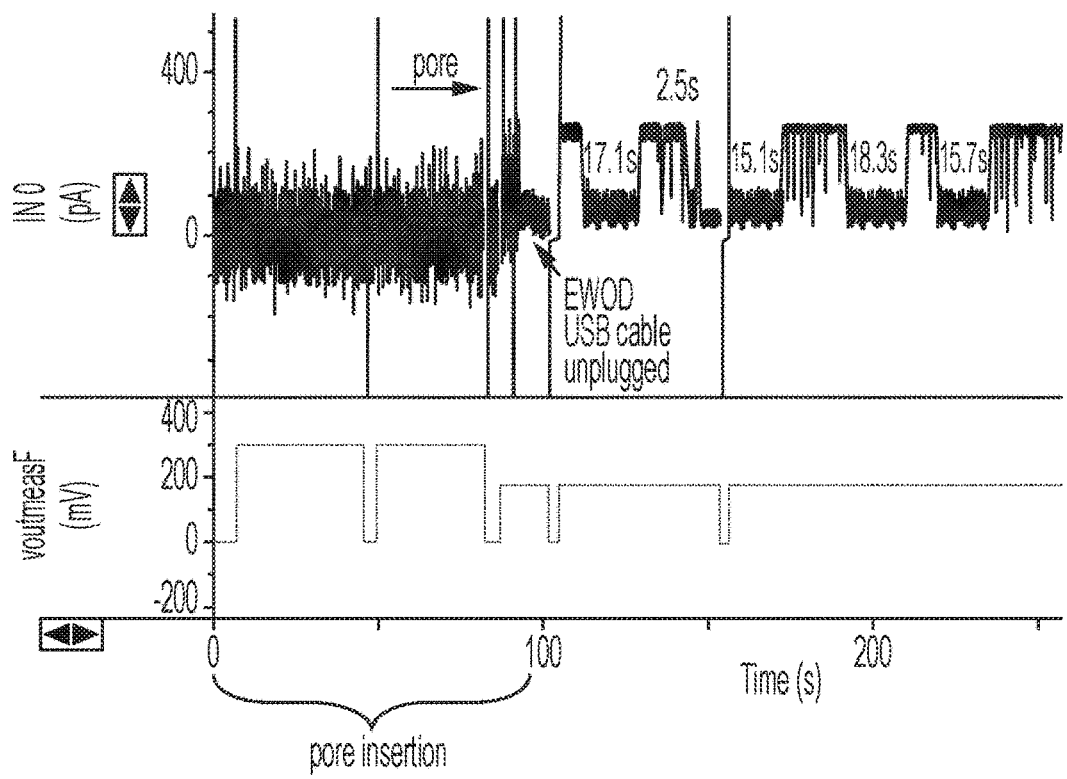
FIG. 24 is, in accordance with certain embodiments, a plot of electrical measurements of current and voltage during an experiment in which DNA translocates through a pore in a system of two droplets in the AM-EWOD device.

The DNA used in this experiment was a standard 3.6 Kb long with a known sequence, so each stand was expected to thread through the pore for a similar amount of time. FIG. 24 shows an example of the electrical measurements taken, showing DNA threading events at 180 mV. Note that the current blockades last from 15.1 to 18.3 seconds, which correlates to roughly 200 bases per second. This is the translocation speed expected for a nanopore operating under the conditions of the experiment. Since each DNA strand in the control sample is identical, the squiggle sequence from each translocation event should be the same.

Figure 25:
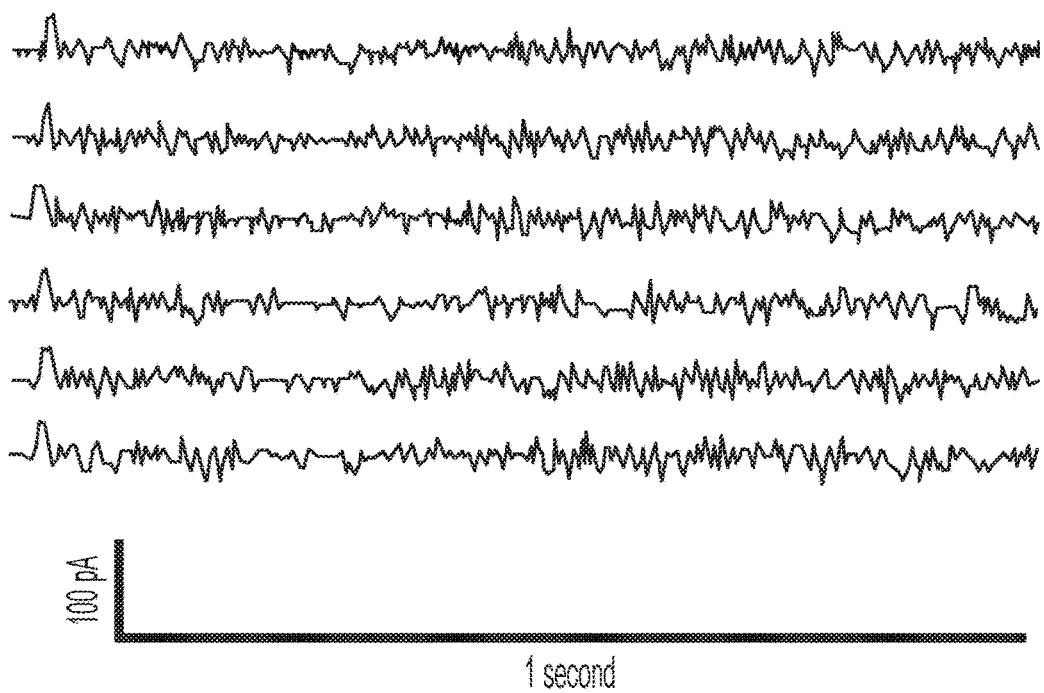
FIG. 25 is, in accordance with certain embodiments, a plot of electrical measurements of current for six translocation events.

FIG. 25 is a plot of expanded current traces for six translocation events, each showing a characteristic "a-basic" peak followed by the sequencing signal. Note that all traces possess the same profile. A rough alignment of these current traces of six translocation events shows that the signal pattern is the same for each strand of DNA.

Example 2

Figure 29A:
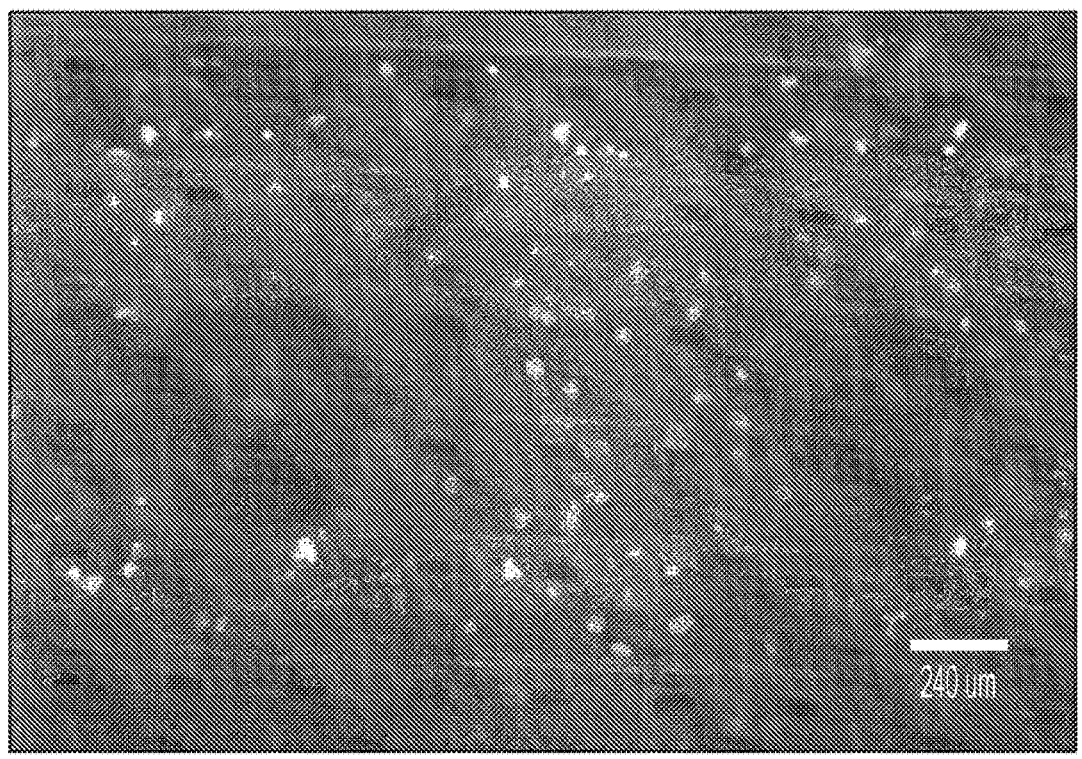
FIGS. 29A and 29B show, in accordance with certain embodiments, two electrodes of an array upon which cells are distributed and then lysed, respectively.
Figure 29B:
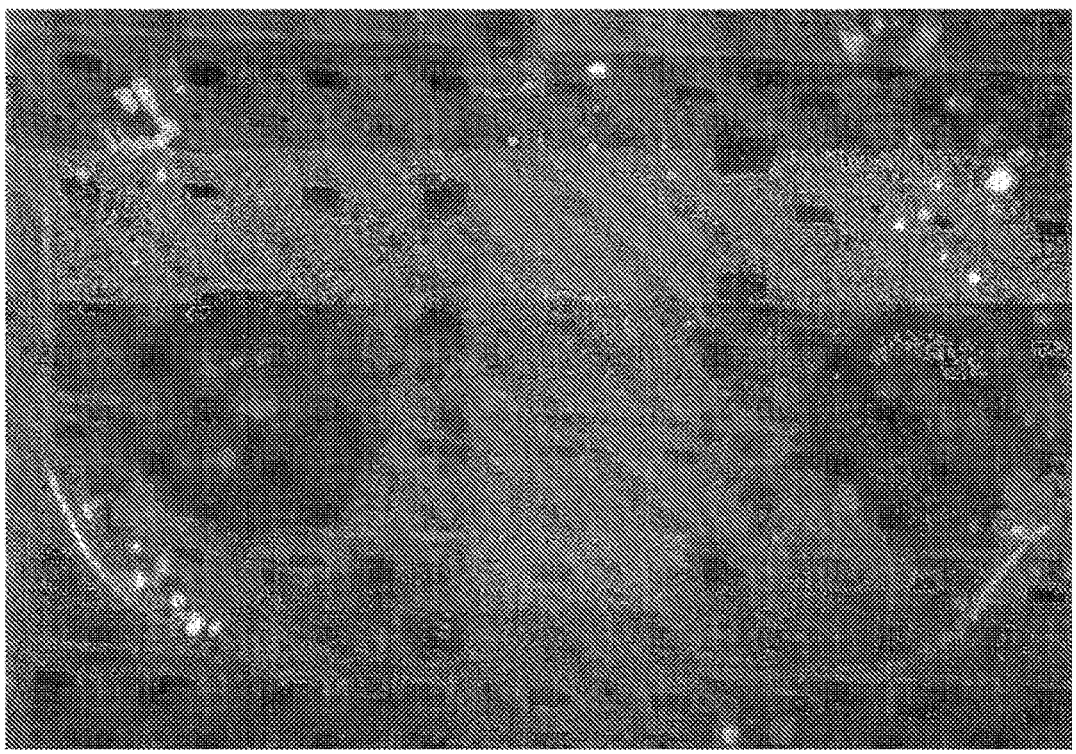

FIGS. 29A and 29B show, in accordance with some embodiments, HeLa cells on an EWOD before and after lysing, respectively. The two slightly darker regions that run vertical on either side of the images are electrodes 48 (i.e., ITO electrodes). The electrodes were used as a lysing station. The dark circles or holes in the middle of each electrode indicate the area where the hydrophobic coating (e.g. Teflon AF) was removed to expose the ITO. The light vertical region in the centre of the images is the ITO free region between the electrodes. Bright spots are HeLa cells. FIG. 27A shows, in accordance with certain embodiments, cells distributed over the electrodes before a lysing signal was applied, while FIG. 27B shows, in accordance with certain embodiments, that there were no intact cells between the electrodes after a lysing signal was applied. Cell lysis was observed as a fading of the GFP fluorescence intensity, which, without wishing to be bound by theory, is presumed to be due to diffusion of GFP and all cytoplasmic contents into the surrounding aqueous solution.

Figure 30A:
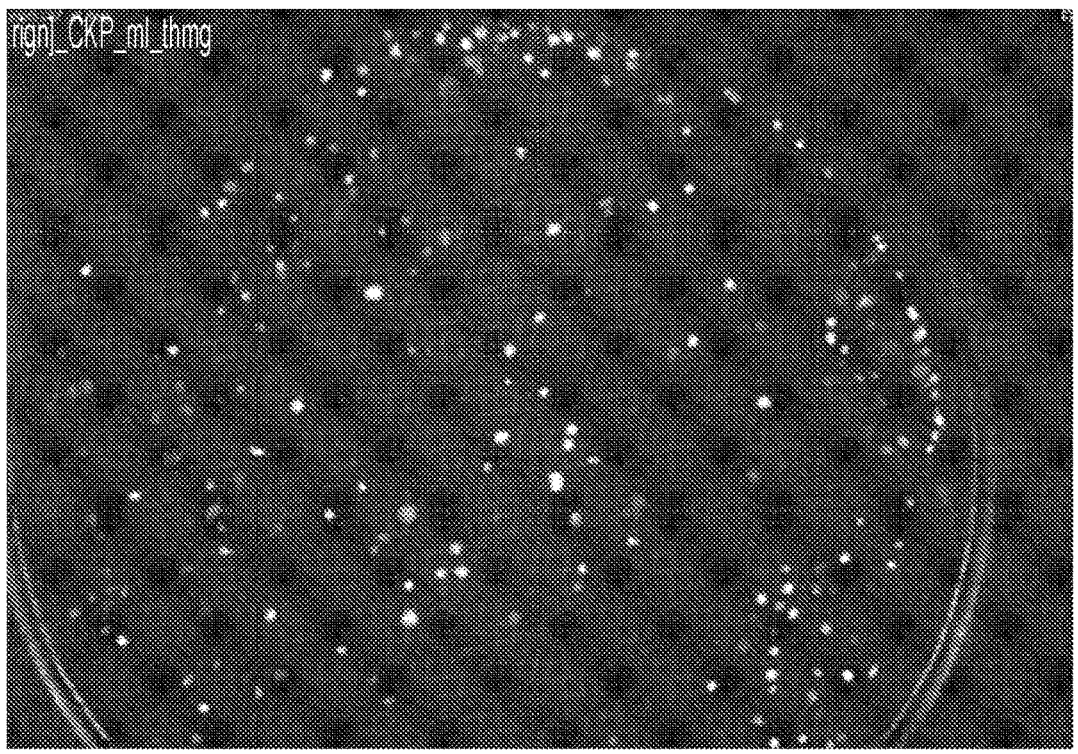
FIG. 30A shows, in accordance with certain embodiments, cells distributed on an EWOD, which are lined up, in accordance with certain embodiments, in FIG. 30B before being lysed, as shown in FIG. 30C.
Figure 30B:
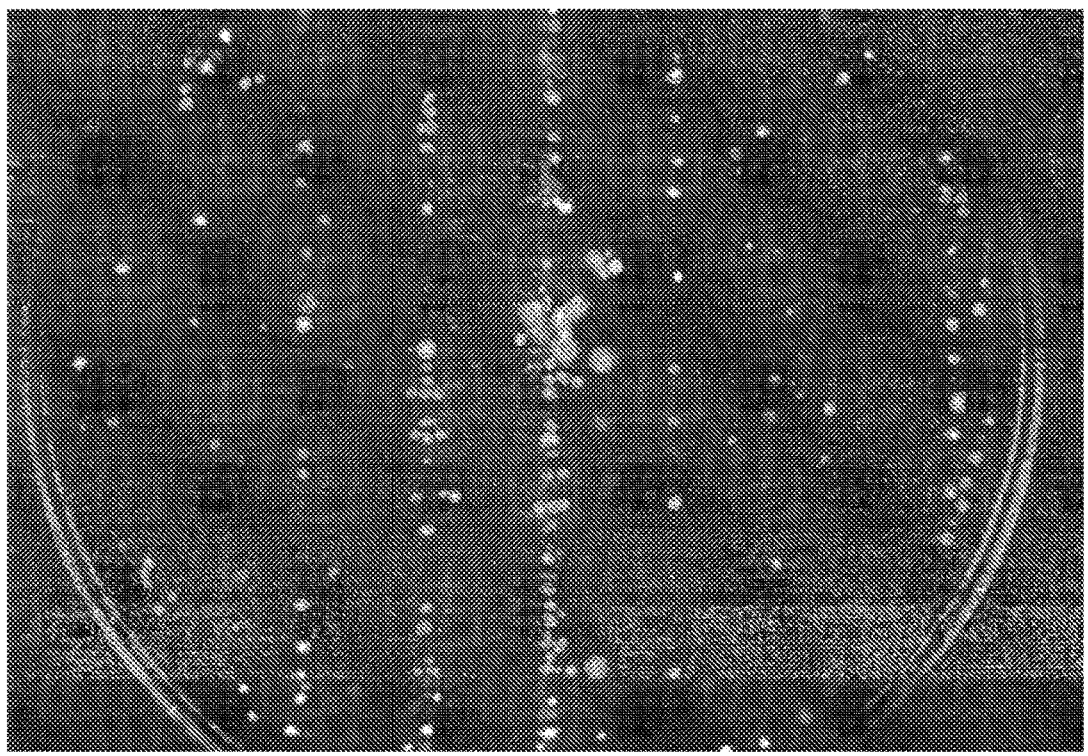
Figure 30C:
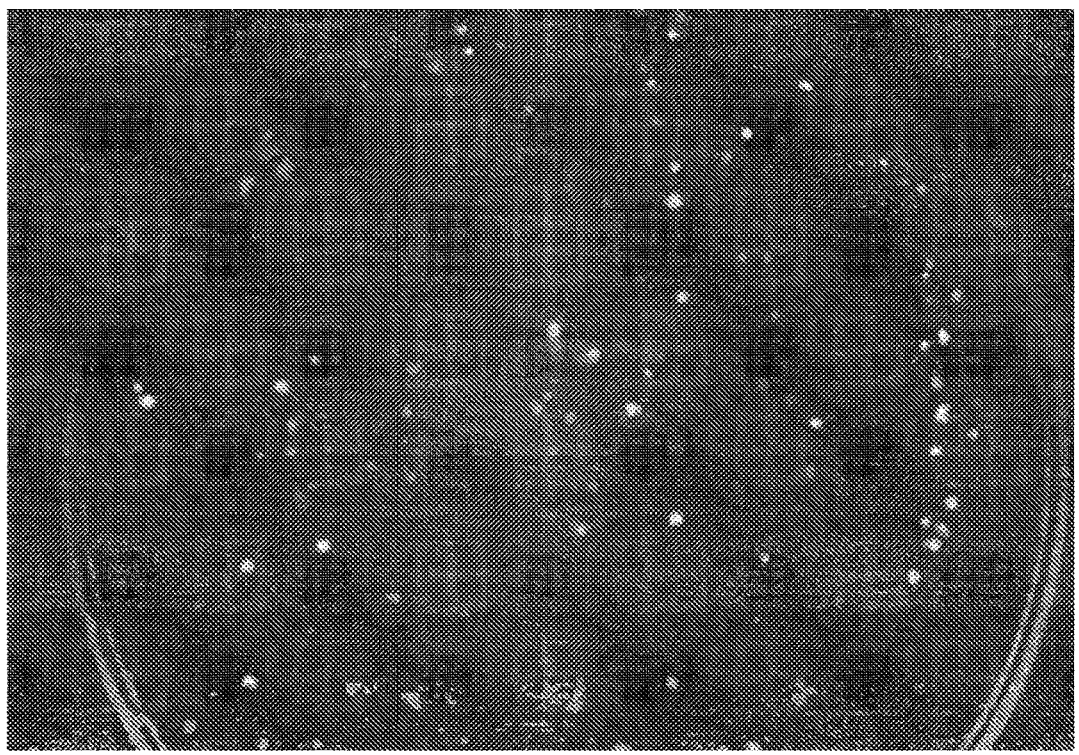

FIGS. 30A to 30C are, in accordance with certain embodiments, views of a chip that had a coating removed to expose the ITO and, thus, does not reveal the dark circles or holes in the middle of each electrode. In some embodiments, using a coating is preferred because it inhibits degradation and/or contamination of the sample with indium and tin oxides and passes less current. FIG. 30A shows, in accordance with certain embodiments, a portion of the apparatus having HeLa cells with green fluorescent protein (GFP) randomly located in a droplet, while FIG. 30B shows, in accordance with certain embodiments, that the apparatus can perform dielectrophoresis to concentrate cells in specific regions within the droplet. In some embodiments, using DEP the cells can be aligned prior to lysis using a lysing signal. This improves the efficiency of the lysing process. FIG. 30C shows, in accordance with certain embodiments, that a number of cells were lysed.

The droplet containing HeLa cells was moved into position under two ITO electrodes. A 7V rms field at 500 kHz was applied to the ITO electrodes on the top plate to drive cells to line up with features in the TFT array, as per FIG. 30B. Once the cells were in position, a 50 ms pulse of 100 V was applied to the ITO electrodes, causing the cells that were lined up to lyse, as shown in FIG. 30C by the absence of the lines shown in FIG. 30C. It is important to note that the cells were lysed without the use of detergents or other reagents. After lysing, DEP can be used to align any unruptured cells within the droplet before lysing is repeated.

Unless defined otherwise, all technical and scientific terms used herein have the same meanings as commonly understood by one of skill in the art to which the disclosed invention belongs. Publications cited herein and the materials for which they are cited are specifically incorporated by reference.

The present invention is described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

In addition, as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein" includes two or more such proteins, reference to "a helicase" includes two or more helicases, reference to "a monomer" refers to two or more monomers, reference to "a pore" includes two or more pores and the like.

In all of the discussion herein, the standard one letter codes for amino acids are used. These are as follows: alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y) and valine (V). Standard substitution notation is also used, i.e. Q42R means that Q at position 42 is replaced with R.

Those skilled in the art will recognize, or be able to ascertain using no more than routine experimentation, many equivalents to the specific embodiments of the invention described herein. Such equivalents are intended to be encompassed by the following claims.

What is claimed is:

1. An apparatus for receiving a droplet having a sample and for lysing said sample to perform experiments on the sample using a plurality of droplet interfaces, the apparatus comprising:
   an electro-wetting device comprising:
   an array of actuation electrodes and an insulator layer covering the actuation electrodes supported on a first substrate and having an outermost hydrophobic surface, the electro-wetting device being arranged to receive a fluid medium and droplets, comprising liquid, in the fluid medium disposed on the hydrophobic surface;
   a control system configured to apply actuation signals to the actuation electrodes selected to manipulate received droplets and to form at least one system of droplets having one or more droplet interfaces between the droplets;
   an array of sensor electrodes coated by a hydrophobic material, said hydrophobic material comprising apertures configured to expose at least part of the sensor electrodes supported on a second substrate, such that the droplets are sandwiched between the first and second substrate;
   a lyser, connected to at least two lysing electrodes, and configured to apply a lysing signal to a droplet for lysing a cell within a droplet, wherein the lysing signal is controlled by the control system; and
   a sensor system configured to take electrical measurements between droplets in a formed system of droplets across droplet interfaces.

2. An apparatus according to claim 1 wherein the at least two lysing electrodes are measurement electrodes or actuation electrodes.

3. An apparatus according to claim 1, wherein the actuation electrodes in the array of actuation electrodes are individually controllable and the control system is configured to pass a lysing signal via a droplet positioned between or over any two actuation electrodes in the array of actuation electrodes.

4. An apparatus according to claim 1, wherein at least two actuation electrodes in the array of actuation electrodes are operable as lysing electrodes configured to provide the lysing signal, and wherein the lysing electrodes are isolated mechanically and/or electrically from the other electrodes in the array of actuation electrodes, and wherein the array of actuation electrodes is configured to manoeuvre a droplet having a sample to and from the lysing electrodes.

5. An apparatus according to claim 1, wherein two lysing electrodes are configured in a lysing zone adjacent or within the array of actuation electrodes, said lysing zone isolated from the array of actuation electrodes, and wherein the array of actuation electrodes is configured to manoeuvre a droplet having a sample to and from the lysing zone.

6. An apparatus according to claim 1, wherein the control system is configured to deactivate and/or isolate the array of actuation electrodes from two or more electrodes in the array of actuation electrodes that operate as lysing electrodes for a period of time during which a lysing signal is applied to a droplet for lysing a cell within a droplet.

7. An apparatus according to claim 6, wherein a ratio between
   the length of time that the control system isolates the array of actuation electrodes, and
   the length of time a lysing signal is applicable to a droplet, is between about 20:1 and about 2:1 in units of seconds: seconds.

8. An apparatus according to claim 1, wherein the second substrate supports at least one lysing electrode.

9. An apparatus according to claim 1, wherein the apparatus is configured to:
   receive a droplet having a sample to be analyzed;
   manoeuvre the droplet to the at least two lysing electrodes for lysing said sample for rupturing cells therein;
   manoeuvre at least a portion of the lysed droplet to a measurement electrode;
   move a second droplet adjacent the lysed droplet to form a droplet interface bilayer; and
   perform measurements on the sample using the droplet interface.

10. An apparatus according to claims 9, wherein following lysing, the apparatus moves and/or mixes the lysed sample for preparation before creating a droplet interface bilayer and subsequent experiments.

11. An apparatus according to claim 9, wherein after manoeuvring the droplet to lysing electrodes the apparatus is further configured to collate content of the droplet in a group using dielectrophoresis such that the group of contents are arranged for lysing for rupturing cells therein.

12. An apparatus according to claim 11 configured to apply the dielectrophoresis field between the lysing electrodes.

13. An apparatus according to claim 3, wherein the electrical measurements are measurements of ion flow between droplets through a transmembrane pore.

14. An apparatus according to claim 3, wherein the sensor system further comprises an analysis system configured to process the electrical measurements, and wherein the analysis system is configured to process the electrical measurements to analyze an analyte that interacts with a transmembrane pore inserted into a formed droplet interface comprising a membrane of amphipathic molecules, and wherein the analyte is a polymer comprising polymer units and the sensor system is configured to process the electrical measurements to derive estimated identities of polymer units of the polymer.

15. An apparatus according to claim 3, wherein the electro-wetting device is arranged to receive droplets comprising amphipathic molecules at their surface and containing a transmembrane pore and the control system is configured to apply actuation signals to the actuation electrodes selected to form at least one system of droplets having one or more droplet interfaces comprising a membrane of amphipathic molecules between the droplets such that a transmembrane pore is allowed to insert into a formed droplet interface.

16. A method for preparing an analyte in an apparatus according to claim 1, the method comprising:
   contacting a first droplet containing a cell of interest with at least two actuation electrodes, said electrodes connectable to the lyser for applying a lysing signal to the first droplet to lyse said cell;
   connecting the lyser to an electrode pair of the at least two actuation electrodes in contact with the first droplet to lyse the cell and release analyte of interest from the cell.

17. The method of claim 16, further comprising using dielectrophoresis to group cells within the droplet prior to lysing.

18. The method of claim 17, wherein the dielectrophoresis is applied between the lysing electrodes in order to group the cells at the lysing electrodes for lysing.

19. The method of claim 18, wherein following lysing of the cells and release of the analyte into the droplet, a further dielectrophoresis field is applied to the droplet to hold the analyte at the at least two lysing electrodes.

20. The method of claim 16, further including:
dividing the first droplet to form a first sub-droplet and a second sub-droplet to form a first droplet pair;
bringing a second droplet in to contact with the first sub-droplet to form a second droplet pair and contacting each of the first sub-droplet and the second droplet with a respective measurement electrode; and
bringing a third droplet in to contact with the second sub-droplet to form a third droplet pair and contacting each of the second sub-droplet and third droplet with a respective measurement electrode.

* * * * *